(12) United States Patent
Zhang et al.

(10) Patent No.: US 7,915,317 B2
(45) Date of Patent: *Mar. 29, 2011

(54) AQUEOUS 2,6-DIISOPROPYLPHENOL PHARMACEUTICAL COMPOSITIONS

(75) Inventors: Zhong Zhang, Sudbury, MA (US); Orn Almarsson, Shrewsbury, MA (US); Hongming Chen, Acton, MA (US)

(73) Assignee: Transform Pharmaceuticals, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/629,308

(22) Filed: Jul. 29, 2003

(65) Prior Publication Data
US 2005/0027019 A1 Feb. 3, 2005

Related U.S. Application Data

(60) Provisional application No. 60/399,490, filed on Jul. 29, 2002, provisional application No. 60/422,195, filed on Oct. 29, 2002, provisional application No. 60/436,979, filed on Dec. 30, 2002, provisional application No. 60/462,450, filed on Apr. 11, 2003, provisional application No. 60/464,314, filed on Apr. 21, 2003, provisional application No. 60/470,403, filed on May 14, 2003, provisional application No. 60/485,354, filed on Jul. 7, 2003.

(51) Int. Cl.
*A61K 31/05* (2006.01)
*A61K 31/14* (2006.01)

(52) U.S. Cl. ...................................... 514/731; 514/643

(58) Field of Classification Search .................. 514/731, 514/643
See application file for complete search history.

(56) References Cited

U.S. PATENT DOCUMENTS

| | | | |
|---|---|---|---|
| 4,056,635 A | 11/1977 | Glen et al. | |
| 4,452,817 A | 6/1984 | Glen et al. | |
| 4,798,846 A * | 1/1989 | Glen et al. | 514/731 |
| 5,296,161 A | 3/1994 | Wiersema et al. | |
| 5,635,540 A | 6/1997 | Edlich et al. | |
| 5,637,625 A | 6/1997 | Haynes | |
| 5,731,355 A | 3/1998 | Jones et al. | |
| 5,962,536 A | 10/1999 | Komer | |
| 5,990,241 A | 11/1999 | Emanuele et al. | |
| 6,077,545 A | 6/2000 | Roskos et al. | |
| 6,100,302 A | 8/2000 | Pejaver et al. | |
| 6,140,373 A | 10/2000 | May et al. | |
| 6,140,374 A | 10/2000 | May et al. | |
| 6,150,423 A * | 11/2000 | Carpenter | 514/731 |
| 6,277,410 B1 | 8/2001 | Kabanov et al. | |
| 6,383,471 B1 | 5/2002 | Chen et al. | |
| 6,534,547 B1 | 3/2003 | Carpenter | |
| 6,623,765 B1 * | 9/2003 | Dennis et al. | 424/502 |
| 6,638,537 B2 | 10/2003 | Dennis et al. | |
| 6,743,436 B1 * | 6/2004 | Lee et al. | 424/423 |
| 7,034,013 B2 | 4/2006 | Thompson et al. | |
| 7,166,303 B2 * | 1/2007 | Meadows et al. | 424/486 |
| 2002/0006442 A1 | 1/2002 | Mishra et al. | |
| 2002/0022667 A1 | 2/2002 | Pace et al. | |
| 2002/0107291 A1 | 8/2002 | De Tommaso | |
| 2003/0138489 A1 | 7/2003 | Meadows et al. | |
| 2003/0165544 A1 | 9/2003 | Mishra et al. | |
| 2004/0220283 A1 | 11/2004 | Zhang et al. | |
| 2004/0265388 A1 | 12/2004 | Zhang et al. | |
| 2005/0009731 A1 | 1/2005 | Desai et al. | |
| 2005/0027019 A1 | 2/2005 | Zhang et al. | |

FOREIGN PATENT DOCUMENTS

| | | |
|---|---|---|
| GB | 2 298 789 A | 9/1996 |
| JP | 2002-521434 | 7/2002 |
| WO | 97/10814 | 3/1997 |
| WO | WO 00/06142 A1 | 2/2000 |
| WO | 00/21517 | 4/2000 |
| WO | WO 00/24376 A1 | 5/2000 |
| WO | 00/78301 | 12/2000 |
| WO | 01/64187 | 9/2001 |
| WO | 01/89514 | 11/2001 |
| WO | WO 01/97779 A2 | 12/2001 |
| WO | WO 01/97796 A1 | 12/2001 |
| WO | WO 02/09671 A2 | 2/2002 |
| WO | WO 02/45709 A1 | 6/2002 |
| WO | WO 02/074200 A1 | 9/2002 |
| WO | 03/017977 | 3/2003 |
| WO | 03/030862 | 4/2003 |
| WO | WO 2004/032910 A | 4/2004 |

OTHER PUBLICATIONS

Adams, Monica L. et al., "Amphiphilic Block Copolymers for Drug Delivery" Journal of Pharm. Sciences, vol. 92, No. 7, Jul. 2003.
Dutta, Sandeep et al., "Formulation-dependent Pharmacokinetics and Pharmacodynamics of Propofol in Rats", J. Pharm. Pharmacol., 1998, 50: 37-42, Aug. 1, 1997.
Ivanova, Rouja et al., "Interaction of Poloxamer Block Copolymers with Cosolvents and Surfactants", Colloids and Surfaces, Physiochemical and Engineering Aspects 183-185 (2001) p. 41-53.
Momot, Konstantin et al., "NMR Study of the Association of Propofol with Nonionic Surfactants", School of Molecular and Microbial Biosciences, University of Sydney, Sydney, NS 2006, Australia, and DBL Australia Pty. Ltd., Level 21, 390 St. Kilda Road, Melbourne, Vic 3004, Austalia.
F.F. Busta et al., Chemical Food Preservatives, Antimicrobial Preservatives and Protectants, Chapter 35, pp. 656-694.
P. Bulet et al., Antimicrobial Peptides in Insects; Structure and Function, Developmental and Comparative Immunology, 23 (1999) 329-344.
Official Action of Aug. 11, 2005 in U.S. Appl. No. 10/766,631 (with attachments).
Amendment and Reply Under 37 CRF §1.111, filed Nov. 8, 2005 in response to Official Action of Aug. 11, 2005 in U.S. Appl. No. 10/766,631..

(Continued)

*Primary Examiner* — Robert C Hayes
*Assistant Examiner* — Shirley V Gembeh
(74) *Attorney, Agent, or Firm* — RatnerPrestia

(57) ABSTRACT

The present invention relates to aqueous pharmaceutical compositions comprising 2,6-diisopropylphenol (propofol). A composition of the present invention can comprise propofol and two or more excipients as an aqueous mixture. The propofol containing compositions are preferably sterile and are parenterally administered to any animal, including humans. The compositions are also chemically and physically stable over a wide range of environmental conditions.

7 Claims, 2 Drawing Sheets

OTHER PUBLICATIONS

Official Action of Feb. 8, 2006 in U.S. Appl. No. 10/766,631.
Amendment filed Jul. 10, 2006 in response to Official Action of Feb. 2, 2006 in U.S. Appl. No. 10/766,631.
Official Action of Oct. 19, 2006 in U.S. Appl. No. 10/766,631.
Amendment filed Jan. 5, 2007 in response to Official Action of Oct. 19, 2006 in U.S. Appl. No. 10/766,631.
Official Action of Sep. 12, 2007 in U.S. Appl. No. 10/766,631 (with attachments).
Amendment filed Nov. 26, 2007 in response to Official Action of Sep. 12, 2007 in U.S. Appl. No. 10/766,631.
Supplemental Response filed Mar. 26, 2008 in response to Applicant's Response of Nov. 26, 2007 in U.S. Appl. No. 10/766,631.
Official Action of Jun. 12, 2008 in U.S. Appl. No. 10/766,631 (with attachments).
Official Action of Jul. 28, 2005 in U.S. Appl. No. 10/677,747 (with attachments).
Amendment and Reply Under 37 CFR §1.111, filed Nov. 28, 2005 in response to Official Action dated Jul. 28, 2005 in U.S. Appl. No. 10/677,747.
Official Action of Jun. 30, 2006 in U.S. Appl. No. 10/677,747.
Amendment under 37 CFR §1.116 filed Sep. 1, 2006 in response to Official Action of Jun. 30, 2006 in U.S. Appl. No. 10/677,747.
Official Action of Dec. 22, 2006 in U.S. Appl. No. 10/677,747 (with attachments).
Amendment under 37 CFR §1.116 filed Feb. 6, 2007 in response to Official Action of Dec. 22, 2006 in U.S. Appl. No. 10/677,747.
Official Action of Jul. 5, 2007 in U.S. Appl. No. 10/677,747 (with attachments).
Amendment filed Oct. 4, 2007 in response to Official Action of Jul. 5, 2007 in U.S. Appl. No. 10/677,747.
Official Action of May 28, 2008 in U.S. Appl. No. 10/677,747.
Challa, R., et al.; "Cyclodextrins in Drug Delivery: An Updated Review"; *AAPS PharmSciTech 2005*; Oct. 14, 2005; pp. E329-E357; 6 (2) Article 43; Department of Pharmaceutics, Faculty of Pharmacy, Hamdard University, New Delhi, India.
Lofisson, T., et al.; "Cyclodextrins in Drug Delivery"; *Expert Opinion Drug Delivery*; 2005; pp. 335-351; 2 (2); Ashley Publications; University of Iceland, Faculty of Pharmacy, Hagi, Hofivallagata, Iceland.
Japan Pharmaceutical Excipients Council edit, Pharmaceutical Excipients Directory, section "propylene glycol," 1994, pp. 114.
Ansley, David M. et al., "High dose propofol enhances red cell antioxidant capacity during CPB in humans," *Can J Anaesth* 1999, 46:7(641-648).
Cheng, Ya-Jung et al., "Small-Dose Propofol Sedation Attenuates the Formation of Reactive Oxigen Species in Tourniquet-Induced Ischemia-Reperfusion Injury Under Spinal Anesthesia," *Anesth Analg 2002*, 94:6(1617-1620).
Daskalopoulos, Rina et al., "Accumulation of Intracellular Ascorbate From Dehydroascorbic Acid by Astrocytes Is Decreased After Oxidative Stress and Restored by Propofol," *GLIA 2002*, 39:124(124-132). .
De La Cruz, J.P. et al., "Antiplatelet effect of the anaesthetic drug propofol: influence of red blood cells and leucocytes," *Br J Pharmacol 1999*, 128:7(1538-1544).
De Riu, P. L. et al., "Disposition of propofol between red blood cells, plasma, brain and cerebrospinal fluid in rabbits," *Eur J Anaesthesiol 2000*, 17:1(18-22).
Ergün, Rüchan et al., "Neuroprotective effects of propofol following global cerebral ischemia in rats," *Neurosurg Rev 2002*, 25:1-2(95-98).
Lin, C. -R. et al., "Effect of thiopental, propofol, and etomidate on vincristine toxicity in PC12 cells," *Cell Biol Toxicol 2002*, 18:1(63-70).
Murphy, P. G. et al., "Effect of propofol and thiopentone on free radical mediated oxidative stress of the erythrocyte," *Br J Anaesth 1996*, 76:4(536-543).
Runzer, Tim D. et al., "Tissue Antioxidant Capacity During Anesthesia: Propofol Enhances In Vivo Red Cell and Tissue Antioxidant Capacity in a Rat Model," *Anesth Analg 2002*, 94:1(89-93).
Wilson, John X. et al., "Free Radicals, Antioxidants, and Neurologic Injury: Possible Relationship to Cerebral Protection by Anesthetics," *J Neurosurg Anesthesia 2002*, 14:1(66-79).
F.F. Busta et al., Chemical Food Preservatives, Antimicrobial Preservatives and Protectants, Chapter 35, pp. 656-694 , Seymour Block, Ed:1983 (3rd edition).
P. Bulet et al., Antimicrobial Peptides in Insects; Structure and Function, Developmental and Comparative Immunology, 23 (1999) 329-344.
Official Action of Nov. 23, 2010 in U.S. Appl. No. 12/333,887.

\* cited by examiner

AQUEOUS 2,6-DIISOPROPYLPHENOL PHARMACEUTICAL COMPOSITIONS

RELATED APPLICATION

This application claims benefit of prior U.S. Provisional Patent Application Nos. 60/399,490 filed Jul. 29, 2002; and 60/422,195 filed on Oct. 29, 2002; and 60/436,979 filed on Dec. 30, 2002; and 60/462,450 filed on Apr. 11, 2003; and 60/464,314 filed on Apr. 21, 2003; and 60/470,403 filed on May 14, 2003; and 60/485,354 filed on Jul. 7, 2003.

BACKGROUND OF THE INVENTION

The compound 2,6-diisopropylphenol (propofol) is a well-known anesthetic agent. The onset of anesthesia is largely controlled by a drug's diffusion rate through the blood-brain barrier. Propofol is lipophilic and this helps the compound to provide rapid anesthetic action. However, this lipophilicity renders propofol, a liquid at room temperature, relatively insoluble in water. As a result, propofol is commonly administered (directly into the bloodstream either by infusion or by bolus injection) as an oil-in-water emulsion, containing a lipid component. Lipids, however, are good substrates for bacterial growth and can also be incompatible with preservatives that are at least somewhat water soluble such as benzyl alcohol. Further, parenteral administration of large volumes of lipid emulsions or administration of lipid emulsions over prolonged periods of time may result in hyperlipidemia.

Despite these shortcomings of oil-in-water emulsions, propofol has been a successful anesthetic and is commercially available as Diprivan® Injectable Emulsion (AstraZeneca; Diprivan® is a trademark of Imperial Chemical Industries PLC) for human administration. Propofol is also marketed for veterinary use as Rapinovet™ Anesthetic Injection (Schering-Plough Animal Heath Corp.; Rapinovet™ is a trademark of Schering-Plough Veterinary Corp.) and as PropoFlo™ Anesthetic Injection (Abbott Laboratories; PropoFlo™ is a trademark of Abbott Laboratories).

Diprivan® Injectable Emulsion is a white, oil-in-water emulsion containing, in addition to 10 milligrams propofol per milliliter of emulsion, 100 mg soybean oil/mL, 22.5 mg glycerol/mL, 12 mg egg lecithin/mL, 0.005% disodium edetate, and sodium hydroxide. Diprivan® Injectable Emulsion is indicated as a single-use parenteral product. Diprivan® contains disodium edetate to retard the growth of microorganisms in the event of accidental extrinsic contamination. Diprivan®, however, can still support the growth of microorganisms. As acknowledged in the product insert, there have been reports in which failure to use antiseptic technique when handling the emulsion was associated with microbial contamination and associated medical complications. Tubing and unused portions of Diprivan® should be discarded after 12 hours because of the potential for microbial growth. Diprivan® must be stored in the narrow temperature range of 4 to 22° C. (Diprivan® Injectable Emulsion Product Insert, AstraZeneca (2001)).

PropoFlo™ Anesthetic Injection is an oil-in water emulsion containing, in addition to 10 milligrams propofol per milliliter of emulsion, 100 mg soybean oil/mL, 22.5 mg glycerol/mL, 12 mg egg lecithin/mL, and sodium hydroxide. Like Diprivan®, PropoFlo™ is capable of supporting the growth of microorganisms. Failure to follow aseptic procedures may result in microbial contamination and associated medical complications. Unused portions of PropoFlo™ should be disposed of within 6 hours of vial entry. (PropoFlo™ Anesthetic Injection Product Insert, Abbott Laboratories (1998)).

Rapinovet™ Anesthetic Injection is a white, oil-in-water emulsion containing, in addition to 10 milligrams propofol per milliliter of emulsion, 100 mg soybean oil/mL, 22.5 mg glycerol/mL, 12 mg egg lecithin/mL, 0.25 mg sodium metabisulfite/mL, and sodium hydroxide. Like Diprivan® and PropoFlo™, Rapinovet™ is capable of supporting the growth of microorganisms. (Rapinovet™ Anesthetic Injection Product Insert, Schering-Plough Animal Health (2000)).

SUMMARY OF THE INVENTION

The present invention relates to aqueous pharmaceutical compositions comprising 2,6-diisopropylphenol (i.e., propofol). A composition of the present invention comprises propofol and one or more excipients as an aqueous mixture. The propofol containing compositions are preferably sterile and are parenterally administered to any animal, including humans. The compositions are chemically and physically stable over a wide range of environmental conditions. Compositions of this invention may contain any GRAS excipient or purified poloxamer, Ammonium acetate, Benzalkonium chloride, Benzethonium chloride, Benzyl alcohol, Brij 35, Brij 97, Calcium gluceptate, ChlorobutanOL, Cremophor EL, Deoxycholate, Diethanolamine, Ethanol, Gamma cyclodextrin, Glycerin, Lactobionic acid, Lysine, Magnesium chloride, Methylparaben, PEG 1000, PEG 300, PEG 3350, PEG 400, PEG 600, Poloxamer 188, Poloxamer 237, Poloxamer 338, Poloxmer 407, Polyoxyethylene 100 stearate, Polyoxyethylene 40 stearate, Polyoxyethylene 50 stearate, Polysorbate 20, Polysorbate 80, Povidone, Propylene Glycol, Sodium acetate, Vitamine E TPGS, Sodium benzoate, and Sodium tartate.

Additionally, in some embodiments, compositions of this invention may contain antimicrobial agents, tonicity modifiers, surfactants, pH modifiers, acids, bases, or a second anesthetic.

In another aspect, the present invention is directed in part to a sterile aqueous pharmaceutical composition comprising 2,6-diisopropylphenol; and one or more excipients wherein the composition is substantially free of glyceryl esters of medium or long chain fatty acids.

Additionally, in one embodiment, a sterile aqueous pharmaceutical composition comprising 2,6-diisopropylphenol, and one or more excipients is disclosed wherein the propofol red blood cell-blood plasma partition coefficient, $K_p$, for the composition is at least about twice the $K_p$ obtained upon administration of a conventional propofol emulsion under the same delivery conditions.

The present invention also relates to methods of administering 2,6-diisopropylphenol to a subject in need of anesthesia comprising intravenously delivering to the subject one of the above mentioned sterile aqueous pharmaceutical compositions. Advantageously, in one embodiment, the invention is also directed to a method of delivering propofol to a subject in need of anesthesia, the method comprising administering to a human or veterinary patient a sterile aqueous pharmaceutical composition, the composition comprising (a) 2,6-diisopropylphenol and (b) one or more excipients wherein the propofol red blood cell-blood plasma partition coefficient, $K_p$, for the composition is at least about twice the $K_p$ obtained upon administration of a conventional propofol emulsion under the same delivery conditions.

Propofol pharmaceutical compositions for parenteral administration that do not contain materials that readily support microorganism growth, such as lipids, are needed. Improved propofol compositions which specifically minimize bacterial growth are needed. Further, it is desirable that such compositions exhibit both physical and chemical stability over a wide range of environmental conditions. Still further, the compositions contain a low concentration of excipients or additives so that undesired excipient associated side effects are mitigated. Further, a need exists for propofol compositions that possess enhanced physical and/or chemical stability or that exhibit stability over prolonged periods of time. A need also exists for a method of administering propofol to a patient in need of anesthesia that minimizes and, preferably, eliminates the costly measures that must be taken to ensure the sterility of conventional propofol compositions. Still further, it is desirable to formulate anesthetic compositions possessing antioxidant activity to decrease the effects of ischemic events during surgical or other procedures thereby enhancing recovery.

DETAILED DESCRIPTION OF THE INVENTION

Figure 1:
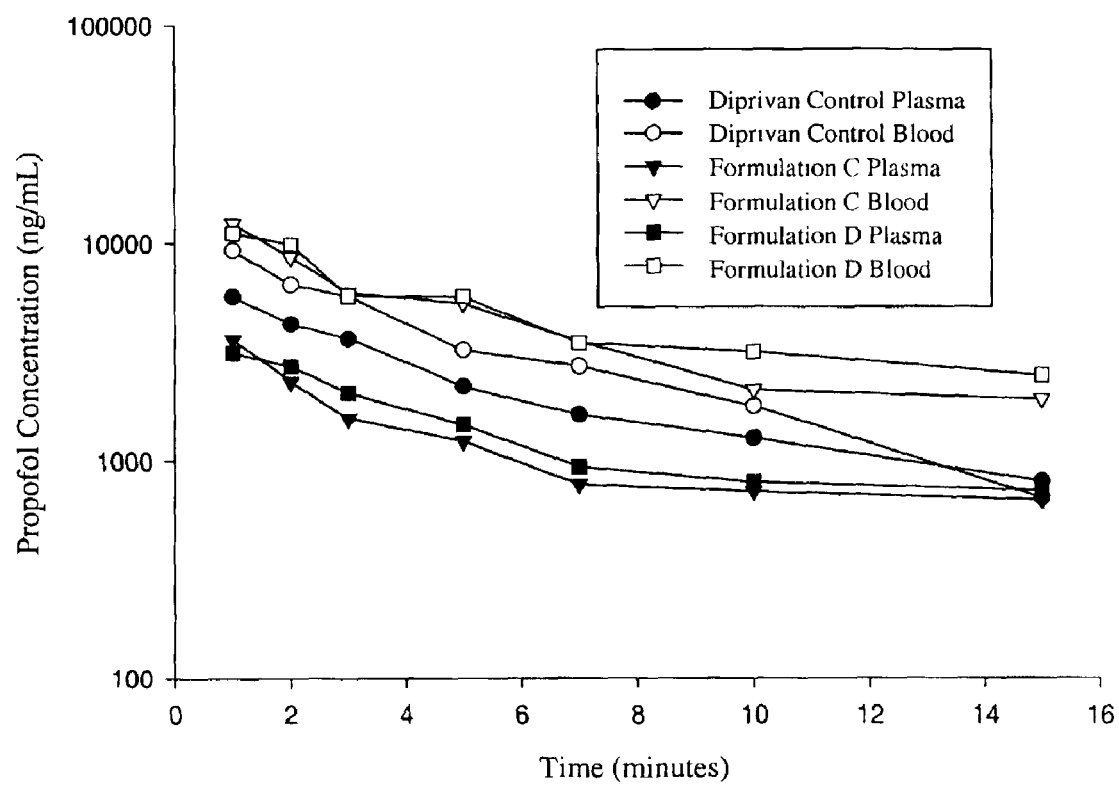
FIG. 1 is a semi-log plot of mean plasma and blood concentrations of propofol (in ng/mL) versus time (in minutes) following administration of single intravenous boluses of two novel propofol compositions (C and D) and Diprivan® Injectable Emulsion control (doses of 10 mg/kg) to Sprague-Dawley male rats.

The present invention relates to aqueous pharmaceutical compositions comprising 2,6-diisopropylphenol (propofol). Compositions of the present invention comprise propofol and one, two, three, four or more excipients as an aqueous mixture. The propofol containing compositions are preferably clear, transparent and sterile and are parenterally administered to any animal, including humans. The compositions are chemically and physically stable over a wide range of environmental conditions. In preferred embodiments, microbial growth is significantly slower when compared to such growth in conventional lipid-containing compositions, in particular, emulsions (e.g., emulsions containing a triacylglycerol and/or a phospholipid).

The term "composition," as used herein, refers to a mixture comprising propofol as an active ingredient and at least one excipient. Compositions of the present invention can be characterized, for example, by their macroscale homogeneity. Macroscale homogenous compositions are characterized by a lack of distinguishable phase separation. Conventional propofol emulsions are milky white in appearance indicating the presence of distinct phases. The oil droplets that scatter light in the conventional emulsions are approximately one micron in size. The compositions of the present invention are clear or sometimes lightly hazy but still transparent. Macroscale homogeneity can be assessed by naked eye visual inspection. Without wishing to be limited to any particular theory, it is likely that the clarity and/or transparency of these compositions indicates propofol solvation in significantly smaller structures than those present in conventional compositions, in particular, oil-in-water propofol emulsions. Applicants base their belief on the results of dynamic light scattering measurements that indicate the presence of nano-scale particles in the compositions of the instant invention such that light scattering is minimized and the system appears as a homogeneous composition.

It is believed that compositions that maintain clarity under visual inspection over time possess a greater degree of thermodynamic stability than that possessed by conventional propofol emulsions. Generally, solutions or mixtures having a high degree of thermodynamic stability tend to maintain particles or particle agglomerations in solution or to preserve their suspension in a liquid over significant periods of time and/or under conditions that do not tend to favor continued solvation or suspension. For example, compositions such as solutions or suspensions that are not thermodynamically favored will eventually exhibit a separation of phases such as a precipitation of solute or suspended matter. Environmental conditions can be selected to maintain thermodynamically disfavored states for longer periods of time. For example, refrigeration is often used to help maintain the suspension of particles in an emulsion.

Typically, the compositions of the present invention maintain the solvation or suspension of their component active agent and excipients over long periods of time (e.g., for at least as long as conventional oil-in-water propofol emulsions) or under conditions more unfavorable to thermodynamic stability (e.g., at higher temperatures). For example, the compositions exhibit naked eye visual clarity at room temperature over extended periods of time. These compositions have been stored at temperatures of up to about 40° C. for up to about 8 weeks with no apparent separation of phases. Phase separation may be assessed microscopically, by light scattering or nephelometry, or by other suitable methods that are well known to those of ordinary skill in the art. Embodiments of the present invention include: an aqueous propofol solution comprising one of the following: a) at least 1%, b) at least 1.5%, or c) at least 2% (w/v) propofol; wherein the total propofol degradants of the solution maintained at one of the following: a) 4° C., b) 8° C., c) 25° C., d) 40° C., or e) 60° C.; at either 65% or 75% relative humidity; for one of the following: 4 weeks, 8 weeks, 13 weeks, 26 weeks, or 1 year; wherein the total propofol degradants is one of the following: less than 5%, 4%, 3%, 2%, 1.5%, 1%, 0.5%, 0.25%, 0.1%, 0.05%, 0.01% total propofol degradants, or not detectable. Each of the preceeding combinations of 1) percent propofol, 2) temperature, 3) percent relative humidity, 4) time, and 5) percent total degradants are included in the present invention as individual species and may be claimed as such.

An "excipient" or "additive," as those terms are used herein, refers to a material contained in a composition other than the primary active ingredient (i.e., propofol) or water. Excipients or additives can be inert or can chemically or physically affect other composition components. Excipients or additives may also have active properties of their own. Excipients can include, but are not limited to, surface active agents (e.g., surfactants, emulsifiers, detergents, binders and wetting agents), salts, polymers, solvents, antimicrobials, preservatives, fillers, diagnostic agents, sugars, alcohols, acids, bases, and buffers. The propofol compositions further comprise active agents in addition to propofol such as, for example, anesthetic and/or antioxidative agents. Alternatively, the propofol compositions are co-administered with compositions comprising additional active agents such as, for example, anesthetic and/or antioxidative agents.

Preferably, the compositions have reduced concentrations of excipients that promote and/or facilitate microbial growth as compared to conventional propofol emulsions or are substantially free of excipients that promote microbial growth. In some embodiments, the compositions are substantially free of lipids and/or oils. In other embodiments, the compositions are free or substantially free of esters of medium or long chain fatty acids (e.g., about $C_6$ to about $C_{25}$ fatty acids) such as glyceryl esters of medium or long chain fatty acids (e.g., mono-, di-, or triacylglycerols). Preferably, the compositions of the instant invention are substantially free of triacylglycerols such as, for example, those contained in vegetable oils (e.g., soybean, castor, sunflower, and arachis oils). In another embodiment, the compositions are free or substantially free of phospholipids (e.g., naturally occurring phospholipids or phospholipids that are synthetically produced or modified).

The term "substantially free," as used herein, refers to compositions that contain the indicated component in only minor amounts, for example, as an impurity accompanying another component or as an impurity produced by a degradation process. Compositions that are substantially free of a component contain that component in a minimal concentration, for example, of less than about 3%, less than about 1%, preferably less than about 0.5%, more preferably less than about 0.1%, or even more preferably less than about 0.05% (w/v) such as less than about 0.01% (w/v).

Generally, the concentration of excipients should be as low as possible to minimize the risk of undesired excipient effects. In some embodiments, the excipient concentration is about equal to or less than about 60%, less than 50%, less than 40%, less than 30%, less than 29%, less than 28%, less than 27%, less than 26%, less than 25%, less than 24%, less than 23%, less than 22%, less than 21%, less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, or less than 3%, (w/v). Low total excipient concentrations are preferred such as, for example, total excipient concentrations less than about 10%, less than about 15% or about 20% (w/v).

Practice of the present invention provides several distinct advantages over conventional propofol compositions, in particular, emulsion formulations. In one aspect, the present invention relates to propofol containing compositions, and their administration to a patient in need of anesthesia, that do not contain triacylglycerols. In another aspect, the propofol containing compositions do not contain phospholipids. Such compositions eliminate the substrate for bacterial growth that those lipids can provide. In contrast, the oil-in-water emulsions of conventional propofol formulations contain lipids such as, for example, soybean oil and lecithin that are able to support the growth of microorganisms. Conventional propofol formulations, composed of lipids, glycerol, and large amounts of water in an isotonic environment with neutral to alkaline pH, provide a medium quite conducive to the growth of many microorganisms. As such, these oil-in-water emulsions require stringent handling, administration, and storage requirements. By reducing or substantially eliminating the presence of triacylglycerols and other microorganism supporting lipids and providing physical and chemical stability, the compositions of the present invention allow for more flexibility in handling, administration, and storage. Less restrictive handling and storage requirements allow for improved and expanded administration options, for example, in remote makeshift hospital settings. Further, the compositions of the present invention, with reduced or no lipid content, minimize, if not eliminate, the potential for contributing to or causing hyperlipidemia.

The aqueous propofol compositions of the invention provide some advantages over other aqueous formulations.

The aqueous propofol compositions of the invention minimize or even eliminate the requirements for antimicrobials, such as disodium edetate, or preservatives such as benzyl alcohol to retard the growth of microorganisms. In addition, these compositions allow for more flexibility and efficiency in administration and packaging. For example, the compositions of the present invention allow packaging to contain multiple doses in contrast to the single dose form of the current commercial propofol emulsions necessitated by sterility concerns. Advantageously, practice of the instant invention allows the withdrawal of multiple doses from a single vial over a period of time. Practice of the present invention also advantageously allows the use of tubing and opened portions of the propofol compositions for longer periods of time, e.g., longer than the currently recommended 12 hours, than are currently possible using conventional propofol compositions such as Diprivan® Injectable Emulsion.

In some embodiments of the present invention the aqueous propofol compositions do comprise an antimicrobial, such as disodium edetate, metabisulfate, or a preservatives such as benzyl alcohol, or an antioxidant such as cysteine or a salt thereof to retard the growth of microorganisms. In this embodiment, the compositions of the present invention comprise a microbiostatic, microbicidal, preservative, or antioxidant (e.g., cysteine or a salt thereof) in a concentration sufficient to exhibit microbiostatic or microbicidal activity against those microorganisms most likely to contaminate the propofol compositions. A further embodiment includes a sterile pharmaceutical composition for parenteral administration which comprises an aqueous solution of propofol, and which further optionally comprises a microbiostatic, microbicidal, preservative, or antioxidant such as cystein (or a salt thereof), EDTA, or metabisulfite, and wherein said aqueous propofol solution is sufficient to prevent no more than a 10-fold increase in growth, or will support no more than a 10-fold increase in growth, of each of *Staphylococcus aureus* ATCC 6538, *Escherichia coli* ATCC 8739, *Pseudomonas aeruginosa* ATCC 9027 and *Candida albicans* ATCC 10231 for at least 24 hours as measured by a test wherein a washed suspension of each said organism is added to a separate aliquot of said composition at approximately 50 colony forming units per ml, at a temperature in the range 20° C. to 25° C., whereafter said aliquots are incubated at 20° C. to 25° C. for 24 hours and thereafter tested for viable counts of said organism. Another embodiment includes a method for producing anaesthesia in a warm-blooded animal which comprises parenterally administering to said animal in need thereof an anaesthetically effective amount of a sterile pharmaceutical composition which comprises an aqueous solution of propofol, and which composition further optionally comprises a microbiostatic, microbicidal, preservative, or antioxidant such as cystein (or a salt thereof), EDTA, or metabisulfite, and wherein said aqueous propofol solution is sufficient to prevent no more than a 10-fold increase in growth, or will support no more than a 10-fold increase in growth, of each of *Staphylococcus aureus* ATCC 6538, *Escherichia coli* ATCC 8739, *Pseudomonas aeruginosa* ATCC 9027 and *Candida albicans* ATCC 10231 for at least 24 hours as measured by a test wherein a washed suspension of each said organism is added to a separate aliquot of said composition at approximately 50 colony forming units per ml, at a temperature in the range 20° C. to 25° C., whereafter said aliquots are incubated at 20° C. to 25° C. for 24 hours and thereafter tested for viable counts of said organism.

Included in the present invention are embodiments wherein the cysteine or salt thereof is present in an aqueous propofol solution at a concentration of about 0.01 to about 2.0, 0.25 to about 1.5, 0.5 to about 1.25, or 0.7 to about 1.0, percent (w/v), or less than 5, less than 4, less than 3, less than 2, less than 1.75, less than 1.5, less than 1.25, less than 1.1, less than 1.0, less than 0.9, less than 0.8, less than 0.7, less than 0.6, less than 0.5, less than 0.4, less than 0.3 or less than 0.2 percent (w/v).

In some embodiments, aqueous compositions of the present invention comprise propofol and at least one, at least two, at least three, or at least four excipients. In one embodiment, propofol is present at a concentration of about 1 to about 25 milligrams per milliliter of composition, more than 1 mg/ml, more than 2 mg/ml, more than 3 mg/ml, more than 4 mg/ml, more than 5 mg/ml, more than 6 mg/ml, more than 7 mg/ml, more than 8 mg/ml, more than 9 mg/ml, more than 10 mg/ml, more than 11 mg/ml, more than 12 mg/ml, more than 13 mg/ml, more than 14 mg/ml, more than 15 mg/ml, more than 16 mg/ml, more than 17 mg/ml, more than 18 mg/ml, more than 19 mg/ml, more than 20 mg/ml, more than 21 mg/ml, more than 22 mg/ml, more than 23 mg/ml, more than 24 mg/ml, more than 25 mg/ml, more than 26 mg/ml, more than 27 mg/ml, more than 28 mg/ml, more than 29 mg/ml, more than 30 mg/ml, more than 31 mg/ml, more than 31 mg/ml, more than 32 mg/ml, more than 33 mg/ml, more than 34 mg/ml, more than 35 mg/ml, more than 36 mg/ml, more than 37 mg/ml, more than 38 mg/ml, more than 39 mg/ml, more than 40 mg/ml, more than 41 mg/ml, more than 42 mg/ml, more than 43 mg/ml, more than 44 mg/ml, more than 45 mg/ml, more than 46 mg/ml, more than 47 mg/ml, more than 48 mg/ml, more than 49 mg/ml, more than 50 mg/ml, more than 60 mg/ml, more than 70 mg/ml, more than 80 mg/ml, more than 90 mg/ml, or more than 100 mg/ml). Alternatively, between about 5 and about 20, about 5 and about 15, or about 8 and about 12 milligrams of propofol per milliliter of composition are present. Preferably, propofol is present at about 9 to about 11 milligrams per milliliter of composition, for example, about 10 mg/ml, or about 15 mg/ml, or about 20 mg/ml, or about 25 mg/ml. Alternatively, propofol compositions can be expressed as propofol percent weight/volume (w/v). For example, compositions of the invention can have propofol compositions of at least 0.5, 0.75, 1.0, 1.25, 1.5, 1.75, 2.0, 2.25, 2.5, 2.75, 3.0, 4, 5, 6, 7, 8, 9, 10, 11, 12, 13, 14, 15, 16, 17, 18, 19, 20, 21, 22, 23, 24, or 25 percent (w/v), or 0.5 to about 2.4, about 0.5 to about 2, about 0.5 to about 1.5, about 0.8 to about 1.2, or, preferably, about 0.9 to about 1.1 percent (w/v).

Further embodiments of the invention include, aqueous propofol compositions comprising at least about 1%, 1.5%, 2% or 2.5% dissolved propofol and an excipient selected from the group consisting of: Ammonium acetate, Benzalkonium chloride, Benzethonium chloride, Benzyl alcohol, Brij 35, Brij 97, Calcium gluceptate, ChlorobutanOL, Cremophor EL, Deoxycholate, Diethanolamine, Ethanol, Gamma cyclodextrin, Glycerin, Lactobionic acid, Lysine, Magnesium chloride, Methylparaben, PEG 1000, PEG 300, PEG 3350, PEG 400, PEG 600, Poloxamer 188, Poloxamer 237, Poloxamer 338, Poloxmer 407, Polyoxyethylene 100 stearate, Polyoxyethylene 40 stearate, Polyoxyethylene 50 stearate, Polysorbate 20, Polysorbate 80, Povidone, Propylene Glycol, Sodium acetate, Vitamine E TPGS, Sodium benzoate, and Sodium tartate.

Excipients, as mentioned above, refer to those materials contained in a composition other than the primary active ingredient or water. Preferably, excipients are suitable for injection into an animal, in particular, a human. Suitable excipients include, but are not limited to, Benzalkonium chloride; Benzethonium chloride; Cremophor EL; Poloxamer 338; Poloxamer 407; Saccharin sodium; polyoxyethylene 20 sorbitan monooleate (i.e., Polysorbate 80 or Tween® 80, Tween® is a trademark of ICI Americas, Inc.); sodium deoxycholate; D-alpha-tocopheryl polyethylene glycol 1000 succinate (i.e., vitamin E TPGS, Eastman Chemical Co.); Poloxamer 237; Poloxamer 188; polyethylene glycol 40 stearate (i.e., PEG-40 stearate); propylene glycol; and polyethylene glycol 400 (i.e., PEG-400).

In addition to excipients such those described above, the compositions further comprise citric acid or a salt thereof. Without being held to any particular theory, Applicants believe that citric acid or a salt thereof in the compositions of the present invention exhibits antioxidant and/or chelating properties. Applicants have discovered that compositions comprising citric acid or a salt thereof possess an unexpectedly high degree of 2,6-diisopropylphenol stability. Also, Applicants have discovered that compositions comprising ascorbic acid or salts thereof unexpectedly display significant 2,6-diisopropylphenol degradation. Thus, citric acid or a salt thereof is added to the compositions of the present invention for its favorable effects including but not limited to modifying pH and/or providing or enhancing (a) antioxidant characteristics, (b) chelating effects of the composition, and/or (c) stability of the excipient(s) or the active agent(s) such as, for example, the 2,6-diisopropylphenol compound. Citric acid or a salt thereof is preferably present in a concentration sufficient to optimize and balance the desired pH and/or the desired antioxidant or chelating properties. In one aspect, the present invention is directed to propofol containing compositions wherein the composition further comprises citric acid or a salt or salts of citric acid in a concentration of at least about 0.05 percent (w/v), in particular, as at least about 0.1 percent (w/v). For example, citric acid is present in the compositions in concentrations of about 0.05 to about 5%, about 0.1 to about 3%, or about 0.1 to about 2% (w/v) or less than 5%, less than 4%, less than 3%, less than 2%, less than 1.75%, less than 1.5%, less than 1.25%, less than 1.1%, less than 1.0%, less than 0.9%, less than 0.8%, less than 0.7%, less than 0.6%, less than 0.5%, less than 0.4%, less than 0.3%, or less than 0.2%, less than 0.15%, less than 0.10%, less than 0.05% (w/v). The invention is also directed to compositions that further comprise a salt or salts of citric acid in a concentration of at least about 0.05 percent (w/v) such as at least about 0.1 percent (w/v). For example, a salt or salts of citric acid are present in the compositions in concentrations of about 0.05 to about 5%, about 0.1 to about 3%, or about 0.1 to about 2% (w/v).

In some embodiments, excipients are present in the propofol containing compositions in the lowest concentrations that will support the formation of a stable composition (e.g., a physically, thermodynamically, and/or chemically stable composition). Keeping excipient concentrations as low as possible helps to minimize the risk of undesired excipient effects. The propofol containing compositions are preferably free of preservatives and/or anti-microbials. Preferably, the compositions are also sterile and pyrogen-free.

The compositions of the present invention preferably have a physiologically neutral pH, such as between about 5 and about 9. The pH of the propofol containing compositions can be adjusted as necessary by, for example, the addition of a base or a salt thereof, for example, an alkali such as sodium hydroxide, potassium hydroxide, or the like. Alternatively, an acid or a salt thereof such as hydrochloric acid, citric acid, or the like can be used to adjust the pH of the compositions. The term "pH modifier," as used herein, refers to substances such as acids, bases, or salts thereof that are used to adjust the pH of a composition and that are well known to those skilled in the art.

In some embodiments, the stability of the compositions of this invention are sensitive to pH. In some compositions, propofol containing compositions have greater stability at a pH of about 5 to 6, at about 4.5 to 6.5, at about 4.5 to 5.5, at about 5 to 7.5 at about 6 to 7, or at about 6.5 to 7.5. The pH of the composition can be adjusted with a pharmaceutically acceptable acid or base to obtain a desired pH. In some embodiments, a specific pH can affect the composition stability or microbial growth.

Pharmaceutical compositions that are intended for application to delicate membranes of the body are commonly adjusted to approximately the same tonicity (i.e., isotonicity) as that of the body fluids. Isotonic compositions are those that cause minimal swelling or contraction of the tissues with which they come in contact, and produce little or no discomfort when instilled in body tissues. Preferably, the propofol compositions are substantially isotonic. The compositions may additionally comprise one or more tonicity modifiers. Examples of tonicity modifiers include, but are not limited to, lactose, dextrose, dextrose anhydrous, mannitol, sodium chloride, potassium chloride, propylene glycol and glycerol.

The propofol containing compositions are preferably provided or administered as sterile pharmaceutical compositions. For example, the propofol containing compositions are administered substantially free of microorganisms. The preparation of sterile pharmaceutical compositions is well known to those experienced in the art. Sterile propofol containing compositions can be prepared using conventional techniques such as, for example, sterilization of final products or aseptic manufacture. In a preferred embodiment, the sterile compositions of the invention are substantially free of microorganisms for a longer period of time after opening than currently available propofol compositions such as Diprivan® Injectable Emulsion.

The compositions of the present invention can be provided in forms that possess desired propofol concentrations and are ready for direct administration to a patient. Alternatively, compositions can be provided in a concentrated form that requires dilution, for example, with water or an injectable solution, prior to administration. In the case of intravenous administration, the compositions can be admixed with diluents suitable for intravenous administration well known to those experienced in the art. Such diluents include water and injectable, aqueous sodium chloride and dextrose solutions. Due to the clear and homogenous character of the compositions of the invention, if further diluted, the resulting diluted compositions are generally also homogeneous and clear.

The present invention is directed to several propofol-containing compositions. In one embodiment, the compositions are substantially microorganism-free pharmaceutical compositions, in particular, sterile aqueous pharmaceutical compositions. Compositions of the instant invention can comprise propofol, water, and one or a combination of two, three, four, or more than four excipients, and water. For example, the excipients can be selected from the group consisting of ammonium acetate, poloxamer (e.g., Poloxamer 237 or Poloxamer 188), polyoxyethylene (23) lauryl ether (e.g., Brij® 35; Brij® is a trademark of ICI Americas, Inc.), polyoxyethylene (10) oleyl ether (e.g., Brij® 97), benzyl alcohol, polysorbate (e.g., polysorbate 20, i.e., polyethylene glycol sorbitan monolaurate (Tween® 20); or polysorbate 80, i.e., polyethylene 20 sorbitan monooleate (Tween® 80)), D-alpha-tocopheryl polyethylene glycol 1000 succinate (i.e., vitamin E TPGS), chlorobutanol, Cremophor® EL (i.e., Polyoxyl 35 Castor Oil; Cremophor® is a trademark of BASF), polyoxyethylene stearate, propylene glycol, deoxycholate (e.g., sodium deoxycholate), diethanolamine, ethanol, glycerin, lactobionic acid, lysine acid, magnesium chloride, polyethylene glycol stearate (e.g., polyethylene glycol 40 stearate, also referred to herein as PEG-40 stearate), and polyethylene glycol (e.g., polyethylene glycol 400, also referred to herein as PEG-400). Any known excipient may be specifically included in the present invention, including the excipients disclosed in *Handbook of Pharmaceutical Additives* compiled by Michael and Irene Ash, Gower Publishing, 1995 (incorporated herein by reference in its entirety).

In some embodiments, the excipient or combination of two, three, four, or more than four excipients is present in the composition in a total concentration of about 1 to about 50%, about 2 to 30%, about 2 to 20%, about 2 to 15%, or about 2 to 10% (w/v), for example, about 8%, less than 40%, less than 30%, less than 29%, less than 28%, less than 27%, less than 26%, less than 25%, less than 24%, less than 23%, less than 22%, less than 21%, less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, or less than 3%, (w/v).

In one aspect, the compositions comprise propofol, a combination of two excipients, and water. The combination of two excipients can be selected, for example, from the group consisting of ammonium acetate and poloxamer; ammonium acetate and polyoxyethylene (23) lauryl ether; benzyl alcohol and poloxamer; polyoxyethylene (23) lauryl ether or polyoxyethylene (10) oleyl ether and poloxamer; polyoxyethylene (23) lauryl ether or polyoxyethylene (10) oleyl ether and polysorbate 20 or 80; polyoxyethylene (23) lauryl ether or polyoxyethylene (10) oleyl ether and D-alpha-tocopheryl polyethylene glycol 1000 succinate; polyoxyethylene (23) lauryl ether and polyoxyethylene (10) oleyl ether; chlorobutanol and poloxamer; Cremophor® EL and poloxamer; Cremophor® EL and polysorbate; Cremophor® EL and polyoxyethylene stearates; Cremophor® EL and propylene glycol; Cremophor® EL and D-alpha-tocopheryl polyethylene glycol 1000 succinate; deoxycholate and D-alpha-tocopheryl polyethylene glycol 1000 succinate; deoxycholate and poloxamer; diethanolamine and D-alpha-tocopheryl polyethylene glycol 1000 succinate; diethanolamine and poloxamer; ethanol and D-alpha-tocopheryl polyethylene glycol 1000 succinate; ethanol and D-alpha-tocopheryl polyethylene glycol 1000 succinate; glycerin and poloxamer; glycerin and D-alpha-tocopheryl polyethylene glycol 1000 succinate; lactobionic acid and poloxamer; lysine acid and poloxamer; magnesium chloride and poloxamer; polyethylene glycol and poloxamer; polyethylene glycol and D-alpha-tocopheryl polyethylene glycol 1000 succinate; polyethylene glycol and polysorbate; polyoxyethlene stearates and polysorbate; polyoxyethlene stearates and D-alpha-tocopheryl polyethylene glycol 1000 succinate; polysorbate and D-alpha-tocopheryl polyethylene glycol 1000 succinate; polysorbate and propylene glycol; and D-alpha-tocopheryl polyethylene glycol 1000 succinate and propylene glycol. Unexpectedly, the above listed combinations of two excipients are able to form clear aqueous propofol compositions with propofol concentrations of up to about 2% (w/v) at about 10% total excipient loading. In preferred embodiments, the total excipient concentration for these compositions is greater than about 1% (w/v) and less than about 40%, 30%, 25%, 20%, 15%, or about 10% (w/v).

In another aspect, the compositions comprise propofol plus a poloxamer. Poloxamers can be selected from poloxamer 124, poloxamer 188, poloxamer 237, poloxamer 338, and poloxamer 407. In addition, poloxamers as described in U.S. Pat. No. 5,990,241 can also be selected. Poloxamers described in U.S. Pat. No. 5,990,241 are purified block copolymers and are defined as "purified poloxamer." The poloxamers and methods of purification described in U.S. Pat. No. 5,990,241 are incorporated herein. Purified poloxamers with narrower ranges of polymer molecular weight composition can be selected for a composition of this invention. Narrower ranges (e.g. compared to commercially available poloxamer 188 or poloxamer 237) of purified poloxamer may have a polydispersity value of, for example, 1.01, 1.02, 1.04, 1.05, 1.1, 1.3, 1.5, 2, 3, or 4. In some embodiments, the polydispersity value of a purified poloxamer is between 5 and 1, between 4 and 1, between 3 and 1, between 2 and 1, between 1.5 and 1, between 1.3 and 1, between 1.2 and 1 or between 1.1 and 1. In some embodiments, a purified poloxamer contains at least 50%, at least 60%, at least 70%, at least 80%, at least 90%, or at least 95% of polymers with a molecular weight between 2000 and 15,000. In some embodiments, a purified poloxamer contains at least 50%, at least 60%, at least 70%, at least 80%, at least 90%, or at least 95% of polymers with a molecular weight between 3000 and 14,000. In some embodiments, a purified poloxamer contains at least 50%, at least 60%, at least 70%, at least 80%, at least 90%, or at least 95% of polymers with a molecular weight between 4000 and 13,000. In some embodiments, a purified poloxamer contains at least 50%, at least 60%, at least 70%, at least 80%, at least 90%, or at least 95% of polymers with a molecular weight between 5000 and 12,000. In some embodiments, a purified poloxamer contains at least 50%, at least 60%, at least 70%, at least 80%, at least 90%, or at least 95% of polymers with a molecular weight between 5000 and 11,000. In some embodiments, a purified poloxamer contains at least 50%, at least 60%, at least 70%, at least 80%, at least 90%, or at least 95% of polymers with a molecular weight between 6000 and 10000. In some embodiments, a purified poloxamer contains at least 50%, at least 60%, at least 70%, at least 80%, at least 90%, or at least 95% of polymers with a molecular weight between 7000 and 9000. In some embodiments, a purified poloxamer contains at least 50%, at least 60%, at least 70%, at least 80%, at least 90%, or at least 95% of polymers with a molecular weight between 7500 and 8500. In some embodiments, a purified poloxamer contains at least 50%, at least 60%, at least 70%, at least 80%, at least 90%, or at least 95% of polymers with a molecular weight between 8000 and 9500.

Included as embodiments of the present invention are compositions or formulations that exclude a specified excipient. Any known excipient, including those disclosed herein or disclosed in *Handbook of Pharmaceutical Additives* compiled by Michael and Irene Ash, Gower Publishing, 1995 (incorporated herein by reference in its entirety), may be specifically excluded from the present invention. Any one or more than one species of excipients may be excluded from the present invention. For e.g., D-alpha-tocopheryl polyethylene glycol 1000 succinate may be excluded from the present invention. Compositions or formulations that comprise a specific excipient exceeding a specified amount may also be excluded. For example, a composition or formulation comprising a specified excipient(s) with a concentration of 90% or more, 80% or more, 70% or more, 60% or more, 50% or more, 40% or more, 30% or more, 29% or more, 28% or more, 27% or more, 26% or more, 25% or more, 24% or more, 23% or more, 22% or more, 21% or more, 20% or more, 19% or more, 18% or more, 17% or more, 16% or more, 15% or more, 14% or more, 13% or more, 12% or more, 11% or more, 10% or more, 9% or more, 8% or more, 7% or more, 6% or more, 5% or more, 4% or more, 3% or more, 2% or more, or 1% or more (w/v) may be specifically excluded from the present invention. For example, the following may be specifically excluded from the present invention: 8% or more, or 10% or more of D-alpha-tocopheryl polyethylene glycol 1000 succinate (w/v); 10% or more or 20% or more of 2-hydroxypropyl-beta-cyclodextrin (w/v); 5% or more, or 30% or more of N-methylpyrrolidone or 2-pyrrolidone, 30% or more of propylene glycol (w/v); combination of either N-methylpyrrolidone or 2-pyrrolidone, and propylene glycol (or a combination of all three), wherein the combined concentration is 60% or more (w/v); 2.5% or more, or 5% or more of a bile acid salt (e.g., sodium glycocolate/glycocolic acid), 4% or more, or 7% or more of lecithin (e.g., soybean or egg), or a combined concentration of 5% or more, or 7.5% or more, or 10% or more of both a bile salt and a lecithin (w/v); 0.5% or more, or 1% or more of benzyl alcohol (w/v); 5% or more, or 15% or more of polyethoxylated castor oil (w/v); 5% or more, 7.5% or more, or 10% or more of a cyclodextrin, such as a sulfoalkyl ether cyclodextrin or sulfobuty ether cyclodextrin. Classes of excipients may also be specifically included or excluded as a component of a composition or formulation of the present invention, and optionally including the concentrations.

As a further embodiment, compositions or formulations of the present invention may be limited to compositions or formulations comprising excipients consisting of excipients; a) certified as GRAS [Generally Recognized as Safe] by the Food and Drug Administration (FDA), b) approved as a food additive pursuant to 21 CFR 171, or c) approved by the FDA for a specific application through a new drug application, and optionally at or below the concentration approved. The compositions or formulations of the present invention may further be limited to compositions or formulations comprising excipients consisting of excipients approved by the FDA for parenteral administration (e.g., i.v.), either generally or as an excipient of a pharmaceutical formulation of a specific drug, through a new drug application, an optionally at or below the concentration approved.

In one embodiment, the composition comprises 2,6-diisopropylphenol; polysorbate (e.g., polyoxyethylene 20 sorbitan monooleate); D-alpha-tocopheryl polyethylene glycol 1000 succinate; and deoxycholate (e.g., sodium deoxycholate). This composition can comprise: (a) propofol as described above; (b) about 1 to about 25%, about 1 to 15%, about 2 to 10%, about 2 to 8%, or about 2 to about 6% (w/v) polyoxyethylene 20 sorbitan monooleate, for example, about 2 to about 4% or about 2 to about 3% (w/v) polyoxyethylene 20 sorbitan monooleate; (c) about 0.5 to about 25%, about 0.5 to 15%, about 1 to 10%, about 1 to 8%, or about 1 to about 5% (w/v) D-alpha-tocopheryl polyethylene glycol 1000 succinate, for example, about 1 to about 3% or about 1 to about 2% (w/v) D-alpha-tocopheryl polyethylene glycol 1000 succinate; (d) about 0.5 to about 3%, about 0.5 to about 2%, about 0.5 to about 1.5%, about 1 to about 25%, about 1 to 15%, about 1 to 10%, about 1 to 5%, about 1 to 3%, about 1 to 2%, about 1.5 to 10%, about 1.5 to 8%, or about 1.5 to about 6% (w/v) sodium deoxycholate, for example, about 1.5 to about 4% or about 1.5 to about 3% (w/v) sodium deoxycholate; and (e) water. In other embodiments, the composition consists essentially of:

(1) water, 2,6-diisopropylphenol, polyoxyethylene 20 sorbitan monooleate, D-alpha-tocopheryl polyethylene glycol 1000 succinate, sodium deoxycholate, optionally, a tonicity modifier, and, optionally, a pH modifier, or stabilizer (e.g., antioxidant such as cystein, chelating agent such as EDTA, or other such as citric acid;

(2) water, 2,6-diisopropylphenol, polyoxyethylene 20 sorbitan monooleate, D-alpha-tocopheryl polyethylene glycol 1000 succinate, sodium deoxycholate, and, optionally, citric acid or a salt thereof; or (3) water, 2,6-diisopropylphenol, polyoxyethylene 20 sorbitan monooleate, D-alpha-tocopheryl polyethylene glycol 1000 succinate, sodium deoxycholate, optionally, citric acid or a salt thereof, and, optionally, a tonicity modifier.

In another embodiment, the composition comprises 2,6-diisopropylphenol, polyethylene glycol 400, poloxamer 188 and propylene glycol. This composition can comprise: (a) propofol as described above; (b) about 1 to about 25%, about 1 to 15%, about 2 to 10%, about 2 to 8%, or about 2 to about 6% (w/v) polyethylene glycol 400, for example, about 3 to about 6% or about 4 to about 6% (w/v) polyethylene glycol 400; (c) about 0.5 to about 25%, about 0.5 to 15%, about 0.5 to 10%, about 0.5 to 8%, or about 0.5 to about 5% (w/v) propylene glycol, for example, about 0.5 to about 3% or about 0.5 to about 2% (w/v) propylene glycol; (d) about 1 to about 25%, about 1 to 15%, about 4 to 12%, about 5 to 10%, or about 6 to about 8% (w/v) poloxamer 188, for example, about 5 to about 9% or about 6 to about 7% (w/v) poloxamer 188; and (e) water. Optionally, benzyl alcohol may be added to this composition in concentrations up to 5%, up to 4%, up to 3%, up to 2%, up to 1% or up to 0.5%.

In other embodiments, the composition consists essentially of:

(1) water, 2,6-diisopropylphenol, poloxamer 188, polyethylene glycol 400, propylene glycol, optionally, a tonicity modifier, and, optionally, a pH modifier, or stabilizer (e.g., antioxidant such as cysteine, chelating agent such as EDTA, or other such as citric acid);

(2) water, 2,6-diisopropylphenol, poloxamer 188, polyethylene glycol 400, propylene glycol, and, optionally, citric acid or a salt thereof; or (3) water, 2,6-diisopropylphenol, poloxamer 188, polyethylene glycol 400, propylene glycol, optionally, citric acid or a salt thereof, and, optionally, a tonicity modifier.

(4) water, 2,6-diisopropylphenol at about 1% (w/v), poloxamer 188 at about 8% (w/v), polyethylene glycol 400 at about 4% (w/v), and propylene glycol at about 1% (w/v).

(5) water, 2,6-diisopropylphenol at about 1% (w/v), poloxamer 188 at about 6% (w/v), polyethylene glycol 400 at about 6% (w/v), and propylene glycol at about 1% (w/v).

(6) water, 2,6-diisopropylphenol at about 1% (w/v), poloxamer 188 at about 6% (w/v), polyethylene glycol 400 at about 4% (w/v), and propylene glycol at about 2% (w/v).

(7) water, 2,6-diisopropylphenol at about 1% (w/v), poloxamer 188 at about 8% (w/v), polyethylene glycol 400 at about 3% (w/v), and propylene glycol at about 1% (w/v).

(8) water, 2,6-diisopropylphenol at about 1% (w/v), poloxamer 188 at about 7% (w/v), polyethylene glycol 400 at about 4% (w/v), and propylene glycol at about 1% (w/v).

(9) water, 2,6-diisopropylphenol at about 1% (w/v), poloxamer 188 at about 7% (w/v), polyethylene glycol 400 at about 3% (w/v), and propylene glycol at about 1% (w/v).

(10) water, 2,6-diisopropylphenol at about 1% (w/v), poloxamer 188 at about 6% (w/v), polyethylene glycol 400 at about 4% (w/v), and propylene glycol at about 1% (w/v).

(11) water, 2,6-diisopropylphenol at about 1% (w/v), poloxamer 188 at about 8% (w/v), polyethylene glycol 400 at about 2% (w/v), and propylene glycol at about 1% (w/v).

In another embodiment, the composition comprises 2,6-diisopropylphenol, polyethylene glycol 400, poloxamer 188, propylene glycol, and citric acid. This composition can comprise: (a) propofol as described above; (b) about 1 to about 25%, about 1 to 15%, about 2 to 10%, about 2 to 8%, or about 2 to about 6% (w/v) polyethylene glycol 400, for example, about 3 to about 6% or about 4 to about 6% (w/v) polyethylene glycol 400; (c) about 0.5 to about 25%, about 0.5 to 15%, about 0.5 to 10%, about 0.5 to 8%, or about 0.5 to about 5% (w/v) propylene glycol, for example, about 0.5 to about 3% or about 0.5 to about 2% (w/v) propylene glycol; (d) about 1 to about 25%, about 1 to 15%, about 4 to 12%, about 5 to 10%, or about 6 to about 8% (w/v) poloxamer 188, for example, about 5 to about 9% or about 6 to about 7% (w/v) poloxamer 188; (e) about 0.5 to 1% citric acid, about 0.5 to 4% citric acid, about 1 to 3% citric acid, about 2 to 5% citric acid, about 1 to 2% citric acid, and (f) water. Optionally, benzyl alcohol may be added to this composition in concentrations up to 5%, up to 4%, up to 3%, up to 2%, up to 1% or up to 0.5%.

In another embodiment, the composition comprises 2,6-diisopropylphenol, polyethylene glycol 400, and poloxamer 188. This composition can comprise: (a) propofol as described above; (b) about 1 to about 25%, about 1 to 15%, about 2 to 10%, about 2 to 8%, or about 2 to about 6% (w/v) polyethylene glycol 400, for example, about 3 to about 6% or about 4 to about 6% (w/v) polyethylene glycol 400; (c) about 1 to about 25%, about 1 to 15%, about 4 to 12%, about 5 to 10%, or about 6 to about 8% (w/v) poloxamer 188, for example, about 5 to about 9% or about 6 to about 7% (w/v) poloxamer 188; and (e) water. Optionally, benzyl alcohol may be added to this composition in concentrations up to 5%, up to 4%, up to 3%, up to 2%, up to 1% or up to 0.5%.

In other embodiments, the composition consists essentially of:

(1) water, 2,6-diisopropylphenol, poloxamer 188, polyethylene glycol 400, optionally, a tonicity modifier, and, optionally, a pH modifier, or stabilizer (e.g., antioxidant such as cysteine, chelating agent such as EDTA, or other such as citric acid;

(2) water, 2,6-diisopropylphenol, poloxamer 188, polyethylene glycol 400, and, optionally, citric acid or a salt thereof; or (3) water, 2,6-diisopropylphenol, poloxamer 188, polyethylene glycol 400, optionally, citric acid or a salt thereof, and, optionally, a tonicity modifier.

(4) water, 2,6-diisopropylphenol at about 1% (w/v), poloxamer 188 at about 8% (w/v), and polyethylene glycol 400 at about 4% (w/v).

(5) water, 2,6-diisopropylphenol at about 1% (w/v), poloxamer 188 at about 8% (w/v), and polyethylene glycol 400 at about 3% (w/v).

(6) water, 2,6-diisopropylphenol at about 1% (w/v), poloxamer 188 at about 7% (w/v), and polyethylene glycol 400 at about 4% (w/v).

(7) water, 2,6-diisopropylphenol at about 1% (w/v), poloxamer 188 at about 7% (w/v), and polyethylene glycol 400 at about 3% (w/v).

(8) water, 2,6-diisopropylphenol at about 1% (w/v), poloxamer 188 at about 6% (w/v), and polyethylene glycol 400 at about 6% (w/v).

(9) water, 2,6-diisopropylphenol at about 1% (w/v), poloxamer 188 at about 9% (w/v), and polyethylene glycol 400 at about 2% (w/v).

Another composition comprises 2,6-diisopropylphenol, polyethylene glycol 400, and a purified poloxamer with an average molecular weight range between about 7600 and 9500. This composition can comprise: (a) propofol as described above; (b) about 1 to about 25%, about 1 to 15%, about 2 to 10%, about 2 to 8%, or about 2 to about 6% (w/v) polyethylene glycol 400, for example, about 3 to about 6% or about 4 to about 6% (w/v) polyethylene glycol 400; (c) about 1 to about 25%, about 1 to 15%, about 4 to 12%, about 5 to 10%, or about 6 to about 8% (w/v) purified poloxamer with an average molecular weight range between about 7600 and 9500, for example, about 5 to about 9% or about 6 to about 7%

(w/v) purified poloxamer with an average molecular weight range between about 7600 and 9500; and (e) water.

Another composition comprises 2,6-diisopropylphenol, polyethylene glycol 400, and a purified poloxamer with an average molecular weight range between about 7600 and 9000. Another composition comprises 2,6-diisopropylphenol, polyethylene glycol 400, and a purified poloxamer with an average molecular weight range between about 8000 and 9000. Another composition comprises 2,6-diisopropylphenol, polyethylene glycol 400, and a purified poloxamer with an average molecular weight range between about 8000 and 8500.

In another embodiment, the composition comprises 2,6-diisopropylphenol, polyethylene glycol 400, a purified poloxamer with an average molecular weight range between about 7600 and 9500 and propylene glycol. This composition can comprise: (a) propofol as described above; (b) about 1 to about 25%, about 1 to 15%, about 2 to 10%, about 2 to 8%, or about 2 to about 6% (w/v) polyethylene glycol 400, for example, about 3 to about 6% or about 4 to about 6% (w/v) polyethylene glycol 400; (c) about 0.5 to about 25%, about 0.5 to 15%, about 0.5 to 10%, about 0.5 to 8%, or about 0.5 to about 5% (w/v) propylene glycol, for example, about 0.5 to about 3% or about 0.5 to about 2% (w/v) propylene glycol; (d) about 1 to about 25%, about 1 to 15%, about 4 to 12%, about 5 to 10%, or about 6 to about 8% (w/v) purified poloxamer, for example, about 5 to about 9% or about 6 to about 7% (w/v) purified poloxamer; and (e) water.

In another embodiment, the composition comprises 2,6-diisopropylphenol, polyethylene glycol 400, a purified poloxamer with an average molecular weight range between about 7600 and 9000 and propylene glycol. In another embodiment, the composition comprises 2,6-diisopropylphenol, polyethylene glycol 400, a purified poloxamer with an average molecular weight range between about 8000 and 9000 and propylene glycol. In another embodiment, the composition comprises 2,6-diisopropylphenol, polyethylene glycol 400, a purified poloxamer with an average molecular weight range between about 8000 and 8500 and propylene glycol.

Another composition comprises polysorbate (e.g., polyoxyethylene 20 sorbitan monooleate), poloxamer (e.g., Poloxamer 237) and polyethylene glycol (PEG) stearate (e.g., PEG-40 stearate). This composition can comprise: (a) propofol as described above; (b) about 1 to about 25%, about 2 to 15%, about 2 to 10%, about 3 to 8%, or about 3 to about 7% (w/v) polyoxyethylene 20 sorbitan monooleate, for example, about 3 to about 5% or about 3 to about 4% (w/v) polyoxyethylene 20 sorbitan monooleate; (c) about 0.5 to about 25%, about 0.5 to 15%, about 0.5 to 10%, about 1 to 8%, or about 1 to about 5% (w/v) Poloxamer 237, for example, about 1 to about 3% or about 1 to about 2% (w/v) Poloxamer 237; (d) about 1 to about 25%, about 1 to 15%, about 1 to 10%, about 1.5 to 8%, or about 1.5 to about 6% (w/v) PEG-40 stearate, for example, about 1.5 to about 4% or about 1.5 to about 3% (w/v) PEG-40 stearate; and (e) water.

The composition can also consist essentially of:
(1) water, 2,6-diisopropylphenol, polyoxyethylene 20 sorbitan monooleate, Poloxamer 237, polyethylene glycol 40 stearate, optionally, a tonicity modifier, and, optionally, a pH modifier;
(2) water, 2,6-diisopropylphenol, polyoxyethylene 20 sorbitan monooleate, Poloxamer 237, polyethylene glycol 40 stearate, and, optionally, citric acid or a salt thereof; or
(3) water, 2,6-diisopropylphenol, polyoxyethylene 20 sorbitan monooleate, Poloxamer 237, polyethylene glycol 40 stearate, optionally, citric acid or a salt thereof, and, optionally, a tonicity modifier.

In another embodiment, the composition comprises polysorbate (e.g., polyoxyethylene 20 sorbitan monooleate), polyethylene glycol (PEG) (e.g., PEG-400) and polyethylene glycol (PEG) stearate (e.g., PEG-40 stearate). This composition can comprise: (a) propofol as described above; (b) about 1 to about 25%, about 2 to 15%, about 2 to 10%, about 3 to 8%, or about 3 to about 7% (w/v) polyoxyethylene 20 sorbitan monooleate, for example, about 3 to about 5% or about 3 to about 4% (w/v) polyoxyethylene 20 sorbitan monooleate; (c) about 2 to about 30%, about 2 to 20%, about 2 to 15%, about 3 to about 10%, or about 3 to about 8% (w/v) PEG-400, for example, about 3 to about 6% or about 3 to about 5% (w/v) PEG-400; (d) about 0.1 to about 25%, about 0.1 to 15%, about 0.2 to 10%, about 0.2 to 6%, or about 0.2 to about 4% (w/v) PEG-40 stearate, for example, about 0.2 to about 1% or about 0.2 to about 0.5% (w/v) PEG-40 stearate; and (e) water.

Alternatively, the composition consists essentially of:
(1) water, 2,6-diisopropylphenol, polyoxyethylene 20 sorbitan monooleate, polyethylene glycol 400, polyethylene glycol 40 stearate, optionally, a tonicity modifier, and, optionally, a pH modifier;
(2) water, 2,6-diisopropylphenol, polyoxyethylene 20 sorbitan monooleate, polyethylene glycol 400, polyethylene glycol 40 stearate, and, optionally, citric acid or a salt thereof; or
(3) water, 2,6-diisopropylphenol, polyoxyethylene 20 sorbitan monooleate, polyethylene glycol 400, polyethylene glycol 40 stearate, optionally, citric acid or a salt thereof and, optionally, a tonicity modifier.

In yet another embodiment, the composition comprises polyethylene glycol (e.g., PEG-400) and poloxamer (e.g., Poloxamer 237). This composition can comprise (a) propofol as described above; (b) about 2 to about 30%, about 3 to about 20%, about 3 to 15%, about 3 to 12%, or about 3 to about 9% (w/v) PEG-400, for example, about 3 to about 7% or about 5 to about 7% (w/v) PEG-400; (c) about 1 to about 25%, about 1 to 15%, about 1 to 10%, about 1 to about 5%, or about 1 to about 3% (w/v) Poloxamer 237, for example, about 1 to about 2% or about 1.1 to about 1.5% (w/v) Poloxamer 237; and (d) water.

In alternative embodiments, the composition also consist essentially of:
(1) water, 2,6-diisopropylphenol, polyethylene glycol 400, Poloxamer 237, optionally, a tonicity modifier, and optionally, a pH modifier;
(2) water, 2,6-diisopropylphenol, polyethylene glycol 400, Poloxamer 237, optionally, and, optionally, citric acid or a salt thereof; or
(3) water, 2,6-diisopropylphenol, polyethylene glycol 400, Poloxamer 237, optionally, citric acid or a salt thereof, and, optionally, a tonicity modifier.

Yet another propofol containing composition of the invention comprises deoxycholate (e.g., sodium deoxycholate) and D-alpha-tocopheryl polyethylene glycol 1000 succinate. This composition can comprise (a) propofol as described above; (b) about 1 to about 25%, about 1 to about 20%, about 1 to 15%, about 1 to 10%, or about 1 to about 5% (w/v) sodium deoxycholate, for example, about 1 to about 3% (w/v) sodium deoxycholate; (c) about 1 to about 25%, about 2 to 15%, about 2 to 10%, about 3 to about 9%, or about 4 to about 8% (w/v) D-alpha-tocopheryl polyethylene glycol 1000 succinate, for example, about 4 to about 6% (w/v) D-alpha-tocopheryl polyethylene glycol 1000 succinate; and (d) water.

Other embodiments consist essentially of:
(1) water, 2,6-diisopropylphenol, sodium deoxycholate, D-alpha-tocopheryl polyethylene glycol 1000 succinate, optionally, a tonicity modifier, and optionally, a pH modifier;

(2) water, 2,6-diisopropylphenol, sodium deoxycholate, D-alpha-tocopheryl polyethylene glycol 1000 succinate, and, optionally, citric acid or a salt thereof; or (3) water, 2,6-diisopropylphenol, sodium deoxycholate, D-alpha-tocopheryl polyethylene glycol 1000 succinate, optionally, citric acid or a salt thereof and, optionally, a tonicity modifier.

Another composition of the invention comprises polysorbate (e.g., polyoxyethylene 20 sorbitan monooleate), propylene glycol, polyethylene glycol (e.g., PEG-400), and poloxamer (e.g., Poloxamer 188). This composition can comprise (a) propofol as described above; (b) about 0.5 to about 25%, about 0.5 to 15%, about 1 to 10%, or about 1 to about 5% (w/v) polyoxyethylene 20 sorbitan monooleate, for example, about 1 to about 3% or about 1 to about 2% (w/v) polyoxyethylene 20 sorbitan monooleate; (c) about 0.5 to about 25%, about 0.5 to 15%, about 0.5 to 10%, about 0.5 to about 5%, about 0.5 to about 3%, about 0.5 to about 2%, about 0.5 to about 1%, or about 1 to about 3% (w/v) propylene glycol, for example, about 1 to about 2% (w/v) propylene glycol; (d) about 1 to about 30%, about 1 to about 20%, about 2 to 15%, or about 2 to about 8% (w/v) PEG-400, for example, about 3 to about 6% or about 4 to about 5% (w/v) PEG-400; (e) about 1 to about 25%, about 1 to 15%, about 2 to 10%, or about 2 to about 8% (w/v) Poloxamer 188, for example, about 3 to about 7% or about 4.5 to about 5.5% (w/v) Poloxamer 188; and (f) water. In some embodiments, this composition further comprises citric acid or a salt thereof. Citric acid can be present in the compositions in concentrations of at least about 0.05 percent (w/v) such as about 0.05 to about 5%, about 0.1 to about 3%, about 0.1 to about 1% (w/v), for example, about 0.1 to about 0.5% or about 0.1 to about 0.2%, or 0.15% (w/v).

These compositions may alternatively consist essentially of:

(1) water, 2,6-diisopropylphenol, polyoxyethylene 20 sorbitan monooleate, propylene glycol, polyethylene glycol 400, Poloxamer 188, optionally, a tonicity modifier, and optionally, a pH modifier;

(2) water, 2,6-diisopropylphenol, polyoxyethylene 20 sorbitan monooleate, propylene glycol, polyethylene glycol 400, Poloxamer 188, and, optionally, citric acid or a salt thereof; or (3) water, 2,6-diisopropylphenol, polyoxyethylene 20 sorbitan monooleate, propylene glycol, polyethylene glycol 400, Poloxamer 188, optionally, citric acid or a salt thereof, and, optionally, a tonicity modifier.

In some embodiments, excipients with similar functional or chemical characteristics can be interchangeable. Thus, in some compositions, variations in one or more excipients are possible. In some embodiments one or more excipients of a composition can be substituted with one or more of a GRAS excipient, purified poloxamer, Ammonium acetate, Benzalkonium chloride, Benzethonium chloride, Benzyl alcohol, Brij 35, Brij 97, Calcium gluceptate, ChlorobutanOL, Cremophor EL, Deoxycholate, Diethanolamine, Ethanol, Gamma cyclodextrin, Glycerin, Lactobionic acid, Lysine, Magnesium chloride, Methylparaben, PEG 1000, PEG 300, PEG 3350, PEG 400, PEG 600, Poloxamer 188, Poloxamer 237, Poloxamer 338, Poloxmer 407, Polyoxyethylene 100 stearate, Polyoxyethylene 40 stearate, Polyoxyethylene 50 stearate, Polysorbate 20, Polysorbate 80, Povidone, Propylene Glycol, Sodium acetate, Vitamine E TPGS, Sodium benzoate, or Sodium tartate. For example, in some compositions, poloxamer 237 may be substituted for poloxamer 188 in a propofol composition while still retaining similar stability characteristics.

In some embodiments, the composition is free from Solutol HS 15, egg lecithin, labrasol, polyoxy 10 oleyl ether, tween, ethanol, or polyethylene glycol. In other embodiments, the composition does not substantially contain micelles greater than 75 um, greater than 60 um, or greater than 50 um. In another embodiment, the composition does not substantially contain micelles less than 50 um, 40 um, or 30 um. In other embodiments, the composition only contains one type of poloxamer, two types of poloxamer, or three types of poloxamer. In other embodiments, the rate of micelle formation or stability is affected by pH or temperature.

In some embodiments, the composition contains benzyl alcohol. In some compositions benzyl alcohol may provide added antimicrobial activity. Benzyl alcohol concentrations can be below 5% w/v, below 4% w/v, below 3% w/v, below 2% w/v, below 1% w/v, below 0.5% w/v, or at 0.45% w/v.

In still another embodiment, a sterile aqueous pharmaceutical composition comprises 2,6-diisopropylphenol, and one or more excipients and wherein the composition is substantially free of triacylglycerols. Alternatively, the composition also is substantially free of other glyceryl esters of medium or long chain fatty acids or phospholipids as described herein. Preferably, at least one excipient of the composition is a surface active agent such as, but not limited to, a surfactant. The propofol compositions of the present invention further comprise active agents in addition to propofol. Additional active agents are useful for purposes such as, for example, reduction or elimination of pain experienced upon administration of the composition to a patient. The propofol containing compositions comprise one or more local anesthetic agents to reduce or eliminate injection pain. If present, local anesthetic agents preferably are present in concentrations sufficient to reduce or eliminate injection pain. Lidocaine is one example of a local anesthetic suitable for use in the instant compositions.

Compositions of the present invention can be formed by mixing 2,6-diisopropylphenol, one or more excipients, and water. Various methods of mixing the composition components are contemplated. Excipients can be mixed into the compositions as neat excipients or as excipients in water. Propofol can be mixed into at least one or more neat excipients or into at least one or more excipients in water. The 2,6-diisopropylphenol may be mixed with at least one or more excipients in water and then combined with either (1) at least one or more neat excipients or (2) with at least one or more excipients mixed in water. In a preferred embodiment, the excipients are mixed together, water is added with mixing, then propofol is added with mixing, and finally, additional water is optionally added to increase the mixture volume. Also preferred, excipients in water are mixed together, propofol is added with mixing, and finally, additional water is optionally added to increase the mixture volume. In most embodiments, propofol is added last.

The water used in the compositions of the present invention is preferably suitable for animal, including human, injection. The water should meet appropriate government and/or health care industry standards. Preferably, the water meets United States Pharmacopeia (USP) 23 standards for Pharmaceutical Grade Water for Injection. Normally, the water should contain no added substances.

Mixing may be performed by any of the various methods known in the art. A mixing apparatus may be batch or continuous. Examples of suitable mixing apparatuses include jet mixers, injectors, mixing nozzles, pumps, agitated line mixers, packed tubes, gas agitated vessels, and stirred vessels, among others. Mixing can be carried out at any temperature that does not substantially degrade the composition components. Typically, mixing is performed at or near room temperature. An advantage of practicing the present invention is the ease by which the compositions can be prepared compared with the methods, such as, for example, microfluidization techniques, often necessary to form propofol compositions, for example, conventional propofol emulsions.

The compositions of the present invention can be characterized by the size of the particles (mean diameter) present in the composition. Without being held to any particular theory, it is believed that in some embodiments the particles contained in the compositions take the form of micelles of various sizes. Alternatively, it is believed that some compositions, or portions of compositions, take the form of micro- or nano-emulsions. The particle size, also herein referred to as the particle geometric size or particle geometric diameter, can be determined using any of the techniques known to those of skill in the art. For example, a Malvern Instruments Zetasizer can be used to determine the size of particles in a composition. The Zetasizer line of measurement systems uses the technique of Photon Correlation Spectroscopy (PCS) to measure submicron particle size. Particles dispersed in a fluid are in constant random motion, commonly referred to as Brownian motion. Photon Correlation Spectroscopy measures the speed of this motion, calculates the diffusion speed of the particles, and relates this to particle size using the Stokes-Einstein equation. One skilled in the art also may employ other suitable means to determine particle size.

In addition to Photon Correlation Spectroscopy (PCS), other methodologies relating to particle size analysis known to those skilled in the art can be employed including, but not limited to, microscopy (e.g., optical and electron), electro-zone or photozone sensing, and other light scattering techniques (e.g., laser diffraction).

In some embodiments, the compositions have an average particle size (mean diameter) less than about 100 nanometers, between about 10 and about 100, between about 25 and about 90 nanometers, or between about 30 and about 75 nanometers. Compositions of the invention consist of particles having a geometric diameter of less than about 90, less than about 75 nanometers, less than about 65 nanometers, less than about 55 nanometers less than about 50 nanometers, less than about 45 nanometers, less than about 40 nanometers, less than about 35 nanometers, less than about 30 nanometers, less than about 25 nanometers, less than about 20 nanometers, less than about 15 nanometers, less than about 10 nanometers, less than about 5 nanometers, or less than about 1 nanometer. In some embodiments, the compositions have an average particle size of between about 50 and 250 nanometers, between about 50 and 150 nanometers, between about 150 and 250 nanometers, and between about 100 and 200 nanometers. In some compositions, all particles have a relatively similar particle size. A relatively similar particle size is defined as the particle size and consistency required of a pharmaceutical product to attain US Food and Drug Administration human drug approval. Optionally, compositions of the present invention are filtered to produce compositions comprising particles of desired sizes or average sizes. Methods for filtering such compositions are well known to those skilled in the art.

In some embodiments, the compositions of this invention have superior clinical benefits compared to currently marketed propofol formulations or other aqueous propofol formulations. Superior clinical benefits can include, but are not limited to, decreased lipid levels, faster onset of action, faster offset of action, decreased damage to red blood cells, and fewer side effects.

The compositions of the invention can be characterized by the chemical stability of the therapeutic, prophylactic or diagnostic agents that comprise the particles. The chemical stability of a constituent anesthetic agent can affect important characteristics of a pharmaceutical composition including shelf-life, proper storage conditions, acceptable environments for administration, biological compatibility, and effectiveness of the agent. Chemical stability can be assessed using techniques well known in the art. For example, assays to detect degradation information obtained from stress studies (e.g., products of acid and base hydrolysis, thermal degradation, photolysis, and oxidation) for both active ingredients and excipients are numerous. One example of a technique that can be used to assess chemical stability is reverse phase high performance liquid chromatography (HPLC).

The compositions of the invention do not exhibit substantial propofol degradation such as, for example, no more than about 5% or no more than about 3% loss of propofol potency at room temperature over a given study period. Alternatively, propofol degradation can be assessed by measuring propofol degradate concentrations such as, for example, quinone and dimer concentrations. In some embodiments, the compositions do not exhibit substantial increases in propofol degradates such as, for example, no more than about 0.05%, no more than about 0.1%, or no more than about 0.2% increase in propofol degradate concentration over a given study period. In a preferred embodiment, any single degradate does not exceed the International Conference on Harmonization (ICH) guidelines, unless specific qualification of that degradate has been performed. (See ICH Document Q3B).

In one embodiment, the compositions do not experience substantial propofol degradation for a period of at least about 6 months when stored refrigerated. Preferably, the compositions do not experience substantial propofol degradation for a period of at least about one year when stored refrigerated. Even more preferred, the compositions do not experience substantial propofol degradation for at least about 6 months, for at least about one year, or, most preferably, for at least about two years when stored at or below about room temperature.

The compositions can be provided, prepared, stored, or transported in any container suitable for maintaining sterility. The container can incorporate means for dispensing an aqueous composition such as, for example, a pierceable or removable seal. The compositions can be dispensed, for example, by extraction with a syringe or by pouring the composition directly into a device (e.g., a syringe, intravenous (IV) bag, or machine) for administration to a patient. Other means for providing, preparing, storing, transporting, and dispensing sterile pharmaceutical compositions are known to those skilled in the art.

In one embodiment, the compositions of the invention are manufactured, packaged, stored, or administered under an oxygen free atmosphere since 2,6-diisopropylphenol is subject to oxidative degradation. Oxygen free atmospheres include nitrogen, argon, or krypton gas, among others. Preferably, the compositions are manufactured, packaged, and stored under a nitrogen gas atmosphere.

The present invention is also directed to methods of administering 2,6-diisopropylphenol to a subject in need of anesthesia, the methods comprising intravenously delivering to the subject a sterile pharmaceutical composition. Sterile pharmaceutical compositions acceptable for delivery to a subject are described herein. In one embodiment, a method is provided for administering 2,6-diisopropylphenol to a subject in need of anesthesia comprising intravenously delivering to the subject a sterile pharmaceutical composition comprising 2,6-diisopropylphenol, and one or more excipients; wherein the composition is substantially free of triacylglycerols. The composition also can be substantially free of other glyceryl esters of medium or long chain fatty acids or phospholipids as described herein. Preferably, at least one excipient of the composition is a surface active agent such as, but not limited to, a surfactant.

The compositions of the present invention can be administered to a patient for the induction and/or maintenance of anesthesia. The compositions can be parenterally administered to any animal, in particular, humans. In one embodiment, administration of a propofol containing composition comprises delivering the composition to a patient as a sole anesthetic, for example, via a bolus injection. In another aspect, administration of a propofol containing composition comprises delivering the composition to a patient for the induction of anesthesia and subsequently maintaining anesthesia with another anesthetic. Alternatively, administration of a propofol containing composition comprises delivering the composition to a patient for the induction and maintenance of longer-term anesthesia, for example, via continuous infusion. Further, the compositions can be delivered to a patient via intramuscular (i.e., IM) means, e.g., IM injection of propofol for induction and/or maintenance of anesthesia as well as other adjunct, desirable properties of compositions of the instant invention as described herein.

The propofol compositions comprise active agents in addition to propofol or, alternatively, the propofol compositions are co-administered with compositions comprising additional active agents. For example, the propofol containing compositions comprise or are co-administered with one or more local anesthetic agents to reduce or eliminate injection pain. If administered, local anesthetic agents preferably are administered in concentrations sufficient to reduce or eliminate injection pain. One of ordinary skill in the art can select and administer concentrations of local anesthetic agent(s) to achieve the desired effects without undue experimentation.

The propofol containing compositions can be administered to a patient using techniques commonly known in the art. For example, the compositions can be delivered intravenously to a patient via bolus injection or by infusion. Infusion of the propofol containing compositions can be made by directly infusing a composition or, alternatively, by addition of a propofol containing composition to an appropriate infusion solution such as 0.9% sodium chloride injection, 5% dextrose injection, or another compatible infusion solution.

In one embodiment, the compositions of the present invention are withdrawn, prior to administration, in multiple doses from a single container such as, for example, a vial or bag. For example, a composition of the invention is resistant to microbial growth even after multiple entries, e.g., with a syringe, into a single vial containing said composition. The multiple doses can be individually, or discretely, withdrawn such as by syringe or continuously withdrawn such as by continuous intravenous infusion. For example, doses of the present compositions are repeatedly withdrawn from a single vial over a course of treatment. Alternatively, a single dose may be withdrawn from a container over a course of treatment.

In one embodiment, the composition of the present invention allows use from a multi-use container. For example, a multi-use container would allow individual doses to be withdrawn from the same container at different time points or different days. Multi-use containers can be fashioned in a variety of structures or methods known in the art. Multi-use containers may be particularly useful for anesthesia of animals.

The quantity of propofol and method of delivery to a patient during administration can be varied, as determined appropriate, by the physician supervising the administration.

In addition to conventional uses of propofol, such as its use in anesthesia, the administration of compositions of the present invention are useful as an antioxidant by administering an effective amount of propofol to a patient in need thereof. If anesthesia is not desired, a sub-anesthetic dose may be administered in many cases. The propofol compositions of the present invention can be used for the prevention or reduction or treatment of oxidative injuries such as ischemia-reperfusion injuries. The propofol compositions can be used to inhibit oxidative damage induced by either hydrophilic or lipophilic radicals. The propofol compositions can be used to protect red blood cells and brain, liver, kidney, heart, lung and skeletal muscle organs, tissue and cells from oxidative stress and injury by pretreatment of an individual with an effective amount of propofol. The propofol compositions of the present invention are also useful to inhibit platelet aggregation by administering an amount of propofol effective to inhibit platelet aggregation. Both the enhancement of antioxidant capacity and antiplatelet effect of propofol, and particularly the propofol compositions of the present invention, make them particularly useful in coronary artery bypass surgery. In this indication propofol may be used, for example, at anesthetizing doses (for e.g., sufentanil 0.3 microg×kg(−1), propofol 1-2.5 mg×kg(−1) bolus then 100 microg×kg(−1) min(−1) before, and 50 microg×kg(−1)×min(−1) during CPB, or sufentanil 0.3 microg×kg(−1), propofol 2-2.5 mg×kg(−1) bolus then 200 microg×kg(−1)×min(−1).

Small-dose propofol sedation can also be used to attenuate the formation of reactive oxygen species, and thus oxidative stress and injury, in tourniquet-induced ischemia-reperfusion injury in patients under spinal anesthesia. An example of this use would be patients undergoing elective total knee replacement under intrathecal anesthesia.

Neuroprotection can further be provided by the propofol compositions, for e.g., by limiting the side-effect of vincristine in cancer therapy; reducing neural damage by attenuating lactate accumulation and oedema formation in focal or global cerebral ischaemia; and reducing oxygen-centered free radical brain injury associated with trauma and stroke.

The propofol compositions of this invention may also be used for sedation. For example, lower doses (e.g. compared to the dose necessary for anesthesia) of propofol can have a sedative effect on a patient. Patients are often sedated during emergency room procedures or prior to surgery to calm the patient.

Methods for administration and assaying the propofol compositions of the invention are routine in the art. Examples of methods of and assays can be found in: Runzer et al. Anesth Analg 2002 January 94(1):89-93; Eur J Anaesthesiol 2000 January 17(1):18-22; De La Cruz J P et al., Br J Pharmacol 1999 December; 128(7):1538-1544; Ansley D M et al., Can J Anaesth 1999 July 46(7):641-648; Murphy P G, et al., Br J Anaesth 1996 April 76(4):536-543; Daskalopoulos R et al. Glia 2002 August 39(2):124-132; Cheng Y J et al. Anesth Analg 2002 June 94(6):1617-1620; Wilson J X et al. J Neurosurg Anesthesiol 2002 January 14(1):66-79; Ergun R et al. Neurosurg Rev 2002 March 25(1-2):95-98; Li C R et al. Cell Biol Toxicol 2002 18(1):63-70.

In one aspect, the invention is directed to a composition of propofol which has a beneficial effect upon hemolysis of blood cells. The compositions of this invention may provide lower red blood cell lysis compared to emulsion propofol compositions, including but not limited to Diprivan. The compositions of this invention may also provide lower red blood cell lysis than saline solution. In a further aspect of this invention, the compositions of this invention may stabilize red blood cell membranes.

In one aspect, the instant invention is directed to a sterile aqueous pharmaceutical composition comprising 2,6-diisopropylphenol, and one or more excipients; wherein the propofol red blood cell-blood plasma partition coefficient ($K_p$) is about 3, is about 4, is about 5, is about 6, is about 7, is about 8, is greater than 3, is greater than 4, is greater than 5, is greater than 6, is greater than 7, is greater than 8, is greater than 9, or is greater than 10. Further, the instant invention is directed to a sterile aqueous pharmaceutical composition comprising 2,6-diisopropylphenol, and one or more excipients; wherein the propofol red blood cell-blood plasma partition coefficient ($K_p$) for the composition is at least about two times, is at least about 3 times, is at least about 4 times, or is at least about 5 times the $K_p$ obtained upon administration of a conventional propofol emulsion (e.g., Diprivan® or Propo-Flo™ or Rapinovet™) under the same delivery conditions. Additionally, the present invention includes a method of delivering propofol to a subject in need of anesthesia, the method comprising administering to a human or veterinary patient the sterile aqueous pharmaceutical composition described above. Preferably, the composition comprises two or more excipients, such as two or more surface active agents (e.g., two or more surfactants). Preferably, the composition is substantially free of triacylglycerols. The composition can be further substantially free of other glyceryl esters of medium or long chain fatty acids or phospholipids. In one embodiment, the propofol red blood cell-blood plasma partition coefficient, $K_p$, for the composition is at least about 3 times the $K_p$ obtained upon administration of a conventional propofol emulsion. In other embodiments, the propofol red blood cell-blood plasma partition coefficient, $K_p$, for the compositions of the instant invention is at least about 3, at least about 4, or at least about 5.

In another aspect, the instant invention is directed to a method of manipulating the blood plasma-red blood cell partition coefficient resulting from administration or delivery of a drug, for example a medicament or a therapeutic, diagnostic, or prophylactic agent such as propofol, to a patient. The blood plasma-red blood cell partition coefficient can be decreased or increased over the blood plasma-red blood cell partition coefficient resulting from administration or delivery of a conventional drug composition to a patient. Alternatively, compositions are prepared using the methods of the present invention that produce higher or lower blood plasma-red blood cell partition coefficients than compositions prepared using other methods. For example, particular formulations of the present invention are likely to increase the blood plasma-red blood cell partition coefficient resulting from administration or delivery of the instant propofol compositions over the blood plasma-red blood cell partition coefficient resulting from administration or delivery of Diprivan® Injectable Emulsion. The blood plasma-red blood cell partition coefficient is, for example, 2 or 3 times higher than the blood plasma-red blood cell partition coefficient resulting from administration or delivery of a conventional drug composition.

The method comprises preparing a pharmaceutical composition that comprises a drug and one or more excipients and wherein the pharmaceutical composition has a concentration of lipid excipients that is lower than the lipid concentration of an alternative composition comprising one or more lipids and wherein the alternative composition produces a lower blood plasma-red blood cell partition coefficient upon administration or delivery to a patient. In one embodiment, the drug is lipophilic (i.e., the drug has an affinity for, tends to combine with, or is capable of dissolving in lipids). In a preferred embodiment, the pharmaceutical composition comprises two or more excipients. Preferably, at least one excipient of the composition is a surface active agent such as, but not limited to, a surfactant. In a preferred embodiment, compositions are prepared that are substantially free of triacylglycerols. In one embodiment, the compositions are substantially free of other glyceryl esters of medium or long chain fatty acids or phospholipids as described herein. In one embodiment, the pharmaceutical composition is substantially free of lipid excipients.

The method comprises manipulating the concentration of lipid excipients to affect the partition of a drug between blood plasma and red blood cells. For example, the concentration of lipid excipients is reduced to increase the amount of drug that enters red blood cells thereby increasing the blood plasma-red blood cell partition coefficient.

Alternatively, the excipients and excipient concentrations of the instant invention can be manipulated to yield a composition that produces a blood plasma-red blood cell partition coefficient that is similar to that achieved by conventional drug formulations such as Diprivan® Injectable Emulsion. The excipients and excipient concentrations also can be manipulated to yield a composition that produces a blood plasma-red blood cell partition coefficient that is lower than that achieved by conventional drug formulations.

Methods for determining the blood plasma-red blood cell partition coefficient for a delivered drug are well known to those of ordinary skill in the art. Preferably, the propofol red blood cell-blood plasma partition coefficient for comparison purposes is obtained upon administration of a conventional propofol emulsion such as, for example, Diprivan® Injectable Emulsion. Diprivan® Injectable Emulsion is a widely available, commercially sold pharmaceutical product. The composition of Diprivan® Injectable Emulsion is also stated herein. Preferably, the conventional propofol emulsion and the composition of the instant invention are delivered under the same conditions. One of ordinary skill in the art can select appropriate experimental conditions and determine the propofol red blood cell-blood plasma partition coefficients ($K_p$) without undue experimentation.

The invention is further illustrated by the following non-limiting exemplification. The contents of all the references cited throughout this application are expressly incorporated herein by reference.

Exemplification

Materials used in making the propofol containing compositions of the following exemplification included: propofol (2,6-diisopropylphenol) (ICN Pharmaceuticals, Inc., Aurora, Ohio); polyoxyethylene 20 sorbitan monooleate (polysorbate 80) (Croda, Inc., Parsippany, N.J.); sodium deoxycholate (Spectrum Quality Products, Inc., Gardena, Calif.); D-alpha-tocopheryl polyethylene glycol 1000 succinate (vitamin E TPGS) (Eastman Chemical Co., Kingsport, Tenn.); Poloxamer 237 (Spectrum Quality Products, Inc., Gardena, Calif.); Poloxamer 188 (Spectrum Quality Products, Inc., Gardena, Calif.); polyethylene glycol 40 stearate (PEG-40 stearate) (Spectrum Quality Products, Inc., Gardena, Calif.); propylene glycol (J. T. Baker, Phillipsburg, N.J.); and polyethylene glycol 400 (PEG-400) (Dow Chemical Co., Midland, Mich.).

EXAMPLE 1

A propofol containing composition (Formulation A) was prepared as follows. Approximately 140 mg sodium deoxycholate, 200 mg polyoxyethylene 20 sorbitan monooleate, and 100 mg D-alpha-tocopheryl polyethylene glycol 1000 succinate were added to a glass vessel. Purified water was added followed by 100 mg propofol. Water was added as necessary to bring the total volume to 10 milliliters. The mixture was stirred at room temperature using a magnetic stirring bar for at least 4 hours over a 24-hour period. The resulting composition was clear to the naked eye with no visible solids present.

EXAMPLE 2

A propofol containing composition (Formulation B) was prepared as follows. Approximately 80 mg Poloxamer 237, 80 mg PEG-40 stearate, and 100 mg polyoxyethylene 20 sorbitan monooleate were added to a glass vessel. Purified water was added followed by 100 mg propofol. Water was added as necessary to bring the total volume to 10 milliliters. The mixture was stirred at room temperature using a magnetic stirring bar for at least 4 hours over a 24-hour period. The resulting composition was clear to the naked eye with no visible solids present.

EXAMPLE 3

A propofol containing composition (Formulation C) was prepared as follows. Approximately 500 mg PEG-400, 350 mg PEG-40 stearate, and 35 mg polyoxyethylene 20 sorbitan monooleate were added to a glass vessel. Purified water was added followed by 100 mg propofol. Water was added as necessary to bring the total volume to 10 milliliters. The mixture was stirred at room temperature using a magnetic stirring bar for at least 4 hours over a 24-hour period. The resulting composition was substantially transparent to the naked eye but slightly hazy.

Laser Light Scattering (LLS) particle size analysis was performed using a Zetasizer 3000HS (Malvern Instruments Inc., Southborough, Mass.). Particle size was determined to be less than approximately 100 nanometers.

EXAMPLE 4

A propofol containing composition (Formulation D) was prepared as follows. Approximately 300 mg Poloxamer 237 and 600 mg PEG-400 were added to a glass vessel. Purified water was added followed by 100 mg propofol. Water was added as necessary to bring the total volume to 10 milliliters. The mixture was stirred at room temperature using a magnetic stirring bar for at least 4 hours over a 24-hour period. The resulting composition was clear to the naked eye with no visible solids present.

EXAMPLE 5

A propofol containing composition (Formulation E) was prepared as follows. Approximately 200 mg sodium deoxycholate and 500 mg D-alpha-tocopheryl polyethylene glycol 1000 succinate were added to a glass vessel. Purified water was added followed by 100 mg propofol. Water was added as necessary to bring the total volume to 10 milliliters. The mixture was stirred at room temperature using a magnetic stirring bar for at least 4 hours over a 24-hour period. The resulting composition was clear to the naked eye with no visible solids present.

EXAMPLE 6

A propofol containing composition (Formulation F) was prepared as follows. 3.0 g polyoxyethylene 20 sorbitan monooleate, 2.9 g propylene glycol, 8.0 g PEG-400, 10.0 g Poloxamer 188, and 0.4 g citric acid were added to a 250 mL volumetric flask. Deionized water was added to the 150 mL marker and the contents of the flask were stirred for 3 hours. Additional deionized water was added to bring the total volume to 197.8 mL and the solution was stirred for one hour. 2.2 mL of 100% pure propofol was added to the flask and the contents of the flask were stirred for at least 8 hours (i.e., until all of the propofol droplets had dissolved). The mixture was filtered through a PVDF filter with a 0.2 micron pore size. The resulting composition was clear to the naked eye. HPLC analysis indicated that less than 1% of propofol was retained by filtration. Since the HPLC assay had a 1-2% variation, this less than 1% loss is not considered significant. Laser Light Scattering (LLS) particle size analysis was performed using a Zetasizer 3000HS (Malvern Instruments Inc., Southborough, Mass.) Particle size was determined to be approximately 20 to 100 nanometers. Physical stability of Formulation F was monitored by measuring mean particle size over the course of a 4 week study. Mean particle size was initially measured as 89±6 nanometers. A sample of Formulation F was held at 60° C. for 4 weeks. At the end of the time period, mean particle size of Formulation F was 84±6 nanometers.

EXAMPLE 7

Propofol containing Formulations C, D and F were prepared as in Examples 3, 4 and 6, respectively. The compositions were separately sealed in glass vials. The compositions then were subjected to a variety of environmental conditions. Reverse phase HPLC was used as an indicator of propofol and excipient chemical stability. HPLC conditions are shown in Table 1 below.

TABLE 1

| HPLC Conditions | |
|---|---|
| Column | Chromolith Performance RP-18e (Merck Kga) 4.6 × 100 mm |
| Mobile Phase | 45% 50 mM KPO$_4$; pH 2.5; acetonitrile |
| Flow Rate | 4.5 mL/min |
| Temperature Column | 35° C. |
| Sample | Ambient |
| Injection Volume | 15 microliters |
| Run Time | 5 minutes |
| Detection | UV, 272 nm |

Prior to HPLC analysis, compositions were held at the indicated conditions for 4 weeks. HPLC was also performed on initially formed compositions. The percent of propofol degradation increase after 4 weeks is summarized in Table 2 below.

TABLE 2

| Increase in the Percent of Total Propofol Degradates after 4 weeks. | | |
|---|---|---|
| Formulation | 25° C. | 40° C. |
| C | 0.50 | 3.7 |
| D | 0.1 | 0.64 |
| F | None detected | 0.07 |

Analysis of degradates is the most sensitive way to gauge stability of relatively stable materials, such as the present propofol compositions, over a short period of time. The temperature increase from 25 to 40° C., the latter temperature representing accelerated conditions, was responsible for increasing amounts of oxidation in each case. The two degradation products detected are likely a quinone and a dimer.

Based on this data, propofol contained in Formulations D and F is predicted to possess stability at room temperature for periods of time greater than 4 weeks. High temperature stability (i.e., at 40° C.) of Formulation F indicates a projected propofol stability of about 1 to 2 years under refrigerated conditions.

EXAMPLE 8

Propofol containing Formulation F was prepared as in Example 6. Samples of the compositions were separately sealed in glass vials and then were held at the temperatures indicated in Table 3 for the indicated amount of time. HPLC analysis of the samples was performed using the methods of Example 7. Table 3 shows the total degradates as percent of peak area by HPLC measured in Formulation F as a function of time and temperature.

TABLE 3

Total degradates (percent of peak area by HPLC) in Formulation F as a function of time and temperature

| Time | Temperature | | |
|---|---|---|---|
| | 25° C. | 40° C. | 60° C. |
| 4 weeks | None detected | None detected | None detected |
| 8 weeks | <0.1 | <0.1 | <0.1 |
| 12 weeks | 0.44 | 1.01 | 1.30 |

The data presented in Table 3 demonstrates that compositions of Formulation F are stable for at least three months.

EXAMPLE 9

Propofol Formulations C and D were made having the same compositions, and prepared by the same methods, as Examples 3 (Formulation C) and 4 (Formulation D). These compositions, along with Diprivan® Injectable Emulsion (AstraZeneca) as a control, were then evaluated in vivo for pharmacokinetic profiles.

Adult male Sprague-Dawley rats were obtained from Charles River Canada, Inc. (St. Constant, Quebec, Canada). At the time of use, the animals each weighed about 250 to 290 grams. The overall design for the animal study is summarized in Table 4.

TABLE 4

In vivo Pharmacokinetic Study Design

| Group | Formulation | Dose (mg/kg) | Dose Volume (mL/kg) | Number of Animals | Samples Collected |
|---|---|---|---|---|---|
| 1 | Control | 10 | 1 | 4 | Plasma |
| 2 | | | | 4 | Blood |
| 3 | C | 10 | 1 | 4 | Plasma |
| 4 | | | | 4 | Blood |
| 5 | D | 10 | 1 | 4 | Plasma |
| 6 | | | | 4 | Blood |

Formulations were administered to the animals by intravenous injection via a jugular vein. The formulations were administered at a dose volume of 1 mL/kg over a period of approximately 1 minute (slow push) via jugular venipuncture under isoflurane anesthesia. As shown in Table 4, each formulation was administered to 2 groups of 4 animals. Animals were randomly selected to fill the study groups on the basis of comparable body weights.

Following administration, blood samples (0.25 to 0.40 mL) were collected by jugular venipuncture under anesthesia from each of the animals at pre-dose (i.e., immediately following completion of dose administration), 2, 3, 5, 7, 10, and 15 minutes from the start of dose administration. The animals were maintained in dorsal recumbancy during both dose administration and during blood sampling.

Blood samples from groups 2, 4, and 6 were stored at −20° C. nominal pending further analysis. Blood samples from groups 1, 3, and 5 were centrifuged at 3200 g at 4° C. nominal for 10 minutes. The resulting plasma samples were harvested and stored at −20° C. nominal pending further analysis.

The animals were observed constantly during dose administration and blood sampling. The time for the animals to regain ventral recumbancy was recorded as an indication of duration of anesthesia. Table 5 shows the mean time to first animal movement and the mean time to regain ventral recumbancy, along with standard deviations, for each of the formulations evaluated.

TABLE 5

Observations on the Effects of Anesthesia

| Group | Formulation | Mean Time to First Movement (min) (S.D.) | Mean Time to Regain Ventral Recumbancy (min) (S.D.) |
|---|---|---|---|
| 1 and 2 | Control | 11.6 (3.9) | 17.5 (4.1) |
| 3 and 4 | C | 13.5 (4.7) | 15.6 (2.2) |
| 5 and 6 | D | 10.8 (4.1) | 14.4 (2.8) |

All plasma and blood samples were analyzed for propofol concentration using LC-MS/MS. Pharmokinetic analysis of propofol in plasma and blood were performed using the PhAST software program (Version 2.3, Phoenix International Life Sciences, Inc, Saint-Laurent, Quebec, Canada).

The area under the concentration-time curve between 0 and 15 minutes ($AUC_{0-15}$) was lower in plasma following administration of the novel propofol compositions (i.e., Formulations C and D) relative to the emulsion control. Propofol clearance (CL) was relatively similar following administration of Formulations C and D and the control. A significant increase in the volume of distribution (Vss) was observed for Formulations C and D from the plasma data (Table 6) and reflects distribution of the drug from plasma into other tissues. An inverse correlation existed between the volume of distribution in plasma and the particle size of the formulations; the emulsion control had micrometer-size droplets while the novel propofol compositions' particles were below 100 nanometers in size. The blood data, obtained by assaying whole blood at each time point for the presence of drug, showed comparable parameters between formulations (Table 7) indicating mass balance of the drug at an equivalent dose. The combined data of Tables 6 and 7 strongly suggest that the nature of the formulation, in particular particle size and availability of propofol to the aqueous medium, plays an important role in determining plasma-blood partitioning of this highly lipophilic drug.

TABLE 6

Mean, ±Standard Deviation, pharmacokinetic parameters of propofol in plasma following a single intravenous dose (10 mg/kg) of a novel propofol formulation (C or D) and a commercially available emulsion formulation in male Sprague-Dawley rats.

| Parameter | Formulation C | Formulation D | Control Emulsion Formulation |
|---|---|---|---|
| $AUC_{0-15}$ (mcg · min/mL) | $14.4 \pm 3.2^\dagger$ | $18.4 \pm 2.2$ | $31.1 \pm 8.9$ |
| CL (mL/min/kg) | $456 \pm 113^\dagger$ | $254 \pm 80$ | $242 \pm 31$ |
| Vss (mL/kg) | $5342 \pm 1145^\dagger$ | $7338 \pm 2748$ | $2595 \pm 612$ |

$^\dagger p < 0.05$ vs Control Emulsion Formulation.

TABLE 7

Mean, ±Standard Deviation, pharmacokinetic parameters of propofol in blood following a single intravenous dose (10 mg/kg) of a novel propofol formulation and a commercially available emulsion formulation in male Sprague-Dawley rats.

| Parameters | Formulation C | Formulation D | Control Emulsion Formulation |
|---|---|---|---|
| $AUC_{0-15}$ (mcg · min/mL) | $62.7 \pm 16^\dagger$ | $60.2 \pm 11$ | $45.5 \pm 6.2$ |
| CL (mL/min/kg) | $112 \pm 20^\dagger$ | $88 \pm 27$ | $192 \pm 30$ |
| Vss (mL/kg) | $1516 \pm 596$ | $1820 \pm 550$ | $1292 \pm 183$ |

$^\dagger p < 0.05$ vs Control Emulsion Formulation.

FIG. 1 shows the mean plasma and blood concentrations of propofol following administration of Formulations C and D and the Diprivan Emulsion control to the male rats.

Figure 2:
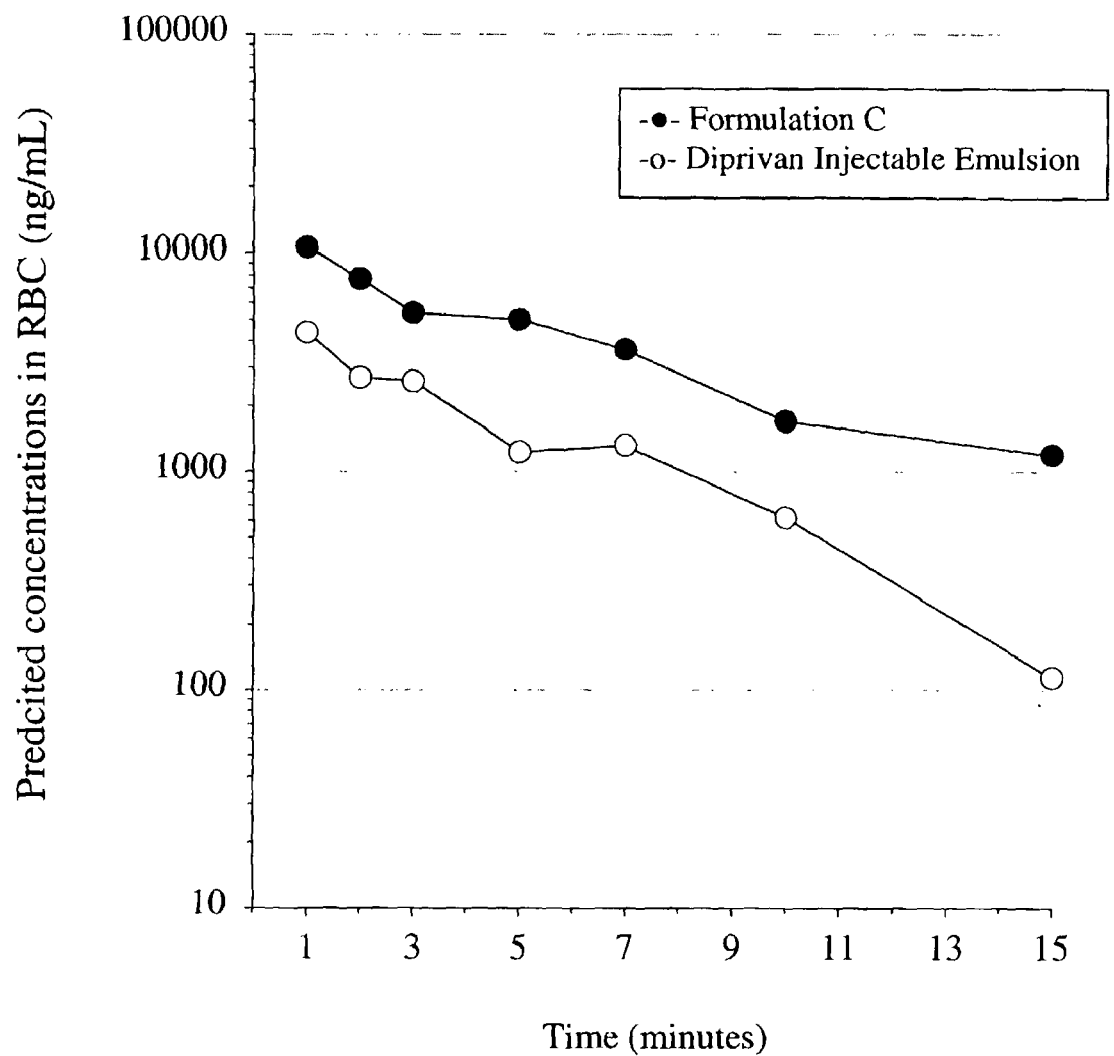
FIG. 2 is a plot of mean predicted propofol concentrations (in ng/mL) in red blood cells (RBC) versus time (in minutes) following single intravenous doses (10 mg/kg) of a novel propofol composition, Formulation C (- -), and a commercially available propofol emulsion, Diprivan® Injectable Emulsion (-o-), in male Sprague-Dawley rats.

Using historical values of red blood cell (RBC) counts in rats, calculations were performed to obtain the area under the concentration-time curve ($AUC_{0-15}$) and the plasma-RBC partition coefficient ($K_p$) for Formulations C and D, as examples of novel propofol compositions, and compared to calculations made for Diprivan® Injectable Emulsion. The fraction of propofol sequestered in RBC with Formulations C and D appear to be markedly higher than that of the emulsion formulation (Table 8). FIG. 2 shows mean predicted propofol concentrations in red blood cells (RBC) versus time following single intravenous doses (10 mg/kg) of Formulation C and Diprivan® Injectable Emulsion in male rats. Following intravenous administration, it appears that propofol from the novel composition concentrates in lipid-rich areas of blood, which participate in the uptake and transfer to its active site and provide anti-platelet and antioxidant activity during anesthesia. Since propofol affinity for whole blood and RBC is an important determinant on the onset, intensity and duration of anesthesia, the results support the hypothesis that the novel composition of propofol can enhance or even optimize the in vivo pharmacological activity of the drug. These results also indicate that additional benefits such as improved resistance of erythrocytes to physical and hemodynamic stress during anesthesia, a greater preservation of red blood cell counts after surgery, and a reduction of reperfusion injury in surgery may be associated with the use of the novel propofol compositions of the present invention.

TABLE 8

Calculated Mean ± Standard Deviation $AUC_{0-15}$ and $K_p$ of propofol in RBC following a single intravenous dose (10 mg/kg) of a novel propofol composition (Formulations C and D) and a commercially available emulsion formulation in male Sprague-Dawley rats.

| Parameters | Formulation C | Formulation D | Diprivan ® Injectable Emulsion |
|---|---|---|---|
| $AUC_{0-15}$ (mcg · min/mL) | $59.0 \pm 20.6^\dagger$ | $59.7 \pm 22.3^\dagger$ | $17.6 \pm 3.0$ |
| $K_p$ (RBC:Plasma) | $8.74 \pm 3.09^\dagger$ | $6.31 \pm 0.89^\dagger$ | $2.03 \pm 0.16$ |

$^\dagger p < 0.05$ vs Diprivan ® Injectable Emulsion.

EXAMPLE 10

Propofol containing compositions were prepared as follows. Excipients listed below were added to a glass vessel. Purified water was added followed by at least 160 mg propofol. Water was added as necessary to bring the total volume to 10 milliliters. The final concentration for each excipient is listed below in parentheses. The mixtures were stirred at room temperature using a magnetic stirring bar for at least 4 hours over a 24-hour period. The resulting compositions were clear to the naked eye with no visible solids present.

1. Benzalkonium chloride (160 mg/ml), Cremophor EL (80 mg/ml);
2. Benzalkonium chloride (160 mg/ml), Poloxamer 237 (80 mg/ml);
3. Benzalkonium chloride (80 mg/ml), Benzethonium chloride (80 mg/ml), Poloxamer 237 (80 mg/ml);
4. Benzalkonium chloride (80 mg/ml), Cremophor EL (80 mg/ml), Polysorbate 80 (80 mg/ml);
5. Benzalkonium chloride (80 mg/ml), Cremophor EL (80 mg/ml), Propylene Glycol (80 mg/ml);
6. Benzalkonium chloride (80 mg/ml), Cremophor EL (80 mg/ml);
7. Benzalkonium chloride (80 mg/ml), PEG 400 (80 mg/ml), Poloxamer 237 (80 mg/ml);
8. Benzalkonium chloride (80 mg/ml), Poloxamer 188 (80 mg/ml), Poloxamer 338 (80 mg/ml);
9. Benzalkonium chloride (80 mg/ml), Poloxamer 188 (80 mg/ml);
10. Benzalkonium chloride (80 mg/ml), Poloxamer 237 (80 mg/ml), Polyoxyethylene 40 Stearate (80 mg/ml);
11. Benzalkonium chloride (80 mg/ml), Poloxamer 237 (80 mg/ml), Polysorbate 80 (80 mg/ml);
12. Benzalkonium chloride (80 mg/ml), Poloxamer 237 (80 mg/ml), Propylene Glycol (80 mg/ml);
13. Benzalkonium chloride (80 mg/ml), Poloxamer 237 (80 mg/ml), vitamine E TPGS (80 mg/ml);
14. Benzalkonium chloride (80 mg/ml), Poloxamer 237 (80 mg/ml), Saccharin sodium (80 mg/ml);
15. Benzalkonium chloride (80 mg/ml), Poloxamer 338 (160 mg/ml);
16. Benzalkonium chloride (80 mg/ml), Poloxamer 338 (80 mg/ml);
17. Benzalkonium chloride (80 mg/ml), Poloxamer 407 (160 mg/ml);
18. Benzalkonium chloride (80 mg/ml), Poloxamer 407 (80 mg/ml), Polyoxyethylene 40 Stearate (80 mg/ml);
19. Benzalkonium chloride (80 mg/ml), Poloxamer 407 (80 mg/ml), Polysorbate 80 (80 mg/ml);
20. Benzalkonium chloride (80 mg/ml), Poloxamer 407 (80 mg/ml), vitamine E TPGS (80 mg/ml);

21. Benzethonium chloride (80 mg/ml), Cremophor EL (160 mg/ml);
22. Benzethonium chloride (80 mg/ml), Cremophor EL (80 mg/ml), PEG 400 (80 mg/ml);
23. Benzethonium chloride (80 mg/ml), Cremophor EL (80 mg/ml), Poloxamer 237 (80 mg/ml);
24. Benzethonium chloride (80 mg/ml), Cremophor EL (80 mg/ml), Poloxamer 338 (80 mg/ml);
25. Benzethonium chloride (80 mg/ml), Cremophor EL (80 mg/ml), Poloxamer 407 (80 mg/ml);
26. Benzethonium chloride (80 mg/ml), Cremophor EL (80 mg/ml), Polysorbate 80 (80 mg/ml);
27. Benzethonium chloride (80 mg/ml), Cremophor EL (80 mg/ml), Propylene Glycol (80 mg/ml);
28. Benzethonium chloride (80 mg/ml), Cremophor EL (80 mg/ml), vitamine E TPGS (80 mg/ml);
29. Benzethonium chloride (80 mg/ml), Cremophor EL (80 mg/ml);
30. Benzethonium chloride (80 mg/ml), PEG 400 (80 mg/ml), Poloxamer 188 (80 mg/ml);
31. Benzethonium chloride (80 mg/ml), PEG 400 (80 mg/ml), Poloxamer 237 (80 mg/ml);
32. Benzethonium chloride (80 mg/ml), PEG 400 (80 mg/ml), Poloxamer 338 (80 mg/ml);
33. Benzethonium chloride (80 mg/ml), PEG 400 (80 mg/ml), Poloxamer 407 (80 mg/ml);
34. Benzethonium chloride (80 mg/ml), PEG 400 (80 mg/ml), Polyoxyethylene 40 Stearate (80 mg/ml);
35. Benzethonium chloride (80 mg/ml), PEG 400 (80 mg/ml), Polysorbate 80 (80 mg/ml);
36. Benzethonium chloride (80 mg/ml), Poloxamer 188 (160 mg/ml);
37. Benzethonium chloride (80 mg/ml), Poloxamer 188 (80 mg/ml), Poloxamer 237 (80 mg/ml);
38. Benzethonium chloride (80 mg/ml), Poloxamer 188 (80 mg/ml), Poloxamer 338 (80 mg/ml);
39. Benzethonium chloride (80 mg/ml), Poloxamer 188 (80 mg/ml), Poloxamer 407 (80 mg/ml);
40. Benzethonium chloride (80 mg/ml), Poloxamer 188 (80 mg/ml), Polyoxyethylene 40 Stearate (80 mg/ml);
41. Benzethonium chloride (80 mg/ml), Poloxamer 188 (80 mg/ml), Polysorbate 80 (80 mg/ml);
42. Benzethonium chloride (80 mg/ml), Poloxamer 188 (80 mg/ml), Propylene Glycol (80 mg/ml);
43. Benzethonium chloride (80 mg/ml), Poloxamer 188 (80 mg/ml), vitamine E TPGS (80 mg/ml);
44. Benzethonium chloride (80 mg/ml), Poloxamer 188 (80 mg/ml);
45. Benzethonium chloride (80 mg/ml), Poloxamer 237 (160 mg/ml);
46. Benzethonium chloride (80 mg/ml), Poloxamer 237 (80 mg/ml), Poloxamer 338 (80 mg/ml);
47. Benzethonium chloride (80 mg/ml), Poloxamer 237 (80 mg/ml), Poloxamer 407 (80 mg/ml);
48. Benzethonium chloride (80 mg/ml), Poloxamer 237 (80 mg/ml), Polyoxyethylene 40 Stearate (80 mg/ml);
49. Benzethonium chloride (80 mg/ml), Poloxamer 237 (80 mg/ml), Polysorbate 80 (80 mg/ml);
50. Benzethonium chloride (80 mg/ml), Poloxamer 237 (80 mg/ml), Propylene Glycol (80 mg/ml);
51. Benzethonium chloride (80 mg/ml), Poloxamer 237 (80 mg/ml), vitamine E TPGS (80 mg/ml);
52. Benzethonium chloride (80 mg/ml), Poloxamer 237 (80 mg/ml);
53. Benzethonium chloride (80 mg/ml), Poloxamer 338 (160 mg/ml);
54. Benzethonium chloride (80 mg/ml), Poloxamer 338 (80 mg/ml), Poloxamer 407 (80 mg/ml);
55. Benzethonium chloride (80 mg/ml), Poloxamer 338 (80 mg/ml), Polyoxyethylene 40 Stearate (80 mg/ml);
56. Benzethonium chloride (80 mg/ml), Poloxamer 338 (80 mg/ml), Polysorbate 80 (80 mg/ml);
57. Benzethonium chloride (80 mg/ml), Poloxamer 338 (80 mg/ml), vitamine E TPGS (80 mg/ml);
58. Benzethonium chloride (80 mg/ml), Poloxamer 338 (80 mg/ml);
59. Benzethonium chloride (80 mg/ml), Poloxamer 407 (160 mg/ml);
60. Benzethonium chloride (80 mg/ml), Poloxamer 407 (80 mg/ml), Polyoxyethylene 40 Stearate (80 mg/ml);
61. Benzethonium chloride (80 mg/ml), Poloxamer 407 (80 mg/ml), Polysorbate 80 (80 mg/ml);
62. Benzethonium chloride (80 mg/ml), Poloxamer 407 (80 mg/ml), Propylene Glycol (80 mg/ml);
63. Benzethonium chloride (80 mg/ml), Poloxamer 407 (80 mg/ml), vitamine E TPGS (80 mg/ml);
64. Benzethonium chloride (80 mg/ml), Poloxamer 407 (80 mg/ml);
65. Benzethonium chloride (80 mg/ml), Polyoxyethylene 40 Stearate (80 mg/ml), Polysorbate 80 (80 mg/ml);
66. Benzethonium chloride (80 mg/ml), Polyoxyethylene 40 Stearate (80 mg/ml), Propylene Glycol (80 mg/ml);
67. Benzethonium chloride (80 mg/ml), Polyoxyethylene 40 Stearate (80 mg/ml), vitamine E TPGS (80 mg/ml);
68. Benzethonium chloride (80 mg/ml), Polyoxyethylene 40 Stearate (80 mg/ml);
69. Benzethonium chloride (80 mg/ml), Polysorbate 80 (160 mg/ml), (80 mg/ml);
70. Benzethonium chloride (80 mg/ml), Polysorbate 80 (80 mg/ml), Propylene Glycol (80 mg/ml);
71. Benzethonium chloride (80 mg/ml), vitamine E TPGS (80 mg/ml);
72. Benzethonium chloride (80 mg/ml), Polysorbate 80 (80 mg/ml);
73. Benzethonium chloride (80 mg/ml), Propylene Glycol (80 mg/ml), vitamine E TPGS (80 mg/ml);
74. Benzethonium chloride (80 mg/ml), vitamine E TPGS (80 mg/ml);
75. Cremophor EL (240 mg/ml);
76. Cremophor EL (160 mg/ml), Polysorbate 80 (80 mg/ml);
77. Cremophor EL (80 mg/ml), Deoxycholate (saturated), Poloxamer 237 (80 mg/ml);
78. Cremophor EL (80 mg/ml), Deoxycholate (saturated), vitamine E TPGS (80 mg/ml);
79. Cremophor EL (80 mg/ml), Poloxamer 407 (160 mg/ml);
80. Deoxycholate (saturated), Poloxamer 237 (160 mg/ml);
81. Deoxycholate (saturated), Poloxamer 237 (80 mg/ml), Poloxamer 338 (80 mg/ml);
82. Deoxycholate (saturated), Poloxamer 237 (80 mg/ml), Poloxamer 407 (80 mg/ml);
83. Deoxycholate saturated), Poloxamer 237 (80 mg/ml), Polysorbate 80 (80 mg/ml);
84. Deoxycholate (saturated), Poloxamer 237 (80 mg/ml), vitamine E TPGS (80 mg/ml);
85. Deoxycholate (saturated), Poloxamer 407 (160 mg/ml);
86. Deoxycholate (saturated), Poloxamer 407 (80 mg/ml), Polysorbate 80 (80 mg/ml);
87. Deoxycholate (saturated), Polysorbate 80 (80 mg/ml), vitamine E TPGS (80 mg/ml);

88. Deoxycholate (saturated), vitamine E TPGS (160 mg/ml);
89. PEG 400 (80 mg/ml), Poloxamer 237 (160 mg/ml);
90. PEG 400 (80 mg/ml), Poloxamer 237 (80 mg/ml), Poloxamer 338 (80 mg/ml);
91. PEG 400 (80 mg/ml), Poloxamer 237 (80 mg/ml), Poloxamer 407 (80 mg/ml);
92. PEG 400 (80 mg/ml), Poloxamer 407 (160 mg/ml);
93. Poloxamer 188 (160 mg/ml), Poloxamer 237 (80 mg/ml);
94. Poloxamer 188 (160 mg/ml), Poloxamer 407 (80 mg/ml);
95. Poloxamer 188 (80 mg/ml), Poloxamer 237 (160 mg/ml);
96. Poloxamer 188 (80 mg/ml), Poloxamer 237 (80 mg/ml), Poloxamer 338 (80 mg/ml);
97. Poloxamer 188 (80 mg/ml), Poloxamer 237 (80 mg/ml), Poloxamer 407 (80 mg/ml);
98. Poloxamer 188 (80 mg/ml), Poloxamer 338 (160 mg/ml);
99. Poloxamer 188 (80 mg/ml), Poloxamer 338 (80 mg/ml), Poloxamer 407 (80 mg/ml);
100. Poloxamer 188 (80 mg/ml), Poloxamer 407 (160 mg/ml);
101. Poloxamer 237 (240 mg/ml);
102. Poloxamer 237 (160 mg/ml), Poloxamer 338 (80 mg/ml);
103. Poloxamer 237 (160 mg/ml), Poloxamer 407 (80 mg/ml);
104. Poloxamer 237 (160 mg/ml), Polyoxyethylene 40 Stearate (80 mg/ml);
105. Poloxamer 237 (160 mg/ml), Polysorbate 80 (80 mg/ml);
106. Poloxamer 237 (160 mg/ml), Propylene Glycol (80 mg/ml);
107. Poloxamer 237 (160 mg/ml), vitamine E TPGS (80 mg/ml);
108. Poloxamer 237 (160 mg/ml), Saccharin sodium (80 mg/ml);
109. Poloxamer 237 (160 mg/ml);
110. Poloxamer 237 (80 mg/ml), Poloxamer 338 (160 mg/ml);
111. Poloxamer 237 (80 mg/ml), Poloxamer 338 (80 mg/ml), Poloxamer 407 (80 mg/ml);
112. Poloxamer 237 (80 mg/ml), Poloxamer 338 (80 mg/ml), vitamine E TPGS (80 mg/ml);
113. Poloxamer 237 (80 mg/ml), Poloxamer 407 (160 mg/ml);
114. Poloxamer 237 (80 mg/ml), Poloxamer 407 (80 mg/ml), Polyoxyethylene 40 Stearate (80 mg/ml);
115. Poloxamer 237 (80 mg/ml), Poloxamer 407 (80 mg/ml), Polysorbate 80 (80 mg/ml);
116. Poloxamer 237 (80 mg/ml), Poloxamer 407 (80 mg/ml), Propylene Glycol (80 mg/ml);
117. Poloxamer 237 (80 mg/ml), Poloxamer 407 (80 mg/ml), Saccharin sodium (80 mg/ml);
118. Poloxamer 237 (80 mg/ml), Poloxamer 407 (80 mg/ml);
119. Poloxamer 237 (80 mg/ml), Polyoxyethylene StearatePolysorbate 80 (80 mg/ml);
120. Poloxamer 237 (80 mg/ml), Polyoxyethylene 40 Stearate (80 mg/ml), vitamine E TPGS (80 mg/ml);
121. Poloxamer 237 (80 mg/ml), Polysorbate 80 (80 mg/ml);
122. Poloxamer 338 (240 mg/ml);
123. Poloxamer 338 (160 mg/ml), Poloxamer 407 (80 mg/ml);
124. Poloxamer 338 (80 mg/ml), Poloxamer 407 (160 mg/ml);
125. Poloxamer 338 (80 mg/ml), Poloxamer 407 (80 mg/ml), Polyoxyethylene 40 Stearate (80 mg/ml);
126. Poloxamer 338 (80 mg/ml), Poloxamer 407 (80 mg/ml), Polysorbate 80 (80 mg/ml);
127. Poloxamer 338 (80 mg/ml), Poloxamer 407 (80 mg/ml), Propylene Glycol (80 mg/ml);
128. Poloxamer 338 (80 mg/ml), Poloxamer 407 (80 mg/ml), vitamine E TPGS (80 mg/ml);
129. Poloxamer 338 (80 mg/ml), Poloxamer 407 (80 mg/ml), Saccharin sodium (80 mg/ml);
130. Poloxamer 338 (80 mg/ml), Poloxamer 407 (80 mg/ml);
131. Poloxamer 338 (80 mg/ml), Polyoxyethylene 40 Stearate (80 mg/ml), Polysorbate 80 (80 mg/ml);
132. Poloxamer 338 (80 mg/ml), Polyoxyethylene 40 Stearate (80 mg/ml), vitamine E TPGS (80 mg/ml);
133. Poloxamer 407 (240 mg/ml);
134. Poloxamer 407 (160 mg/ml), Polyoxyethylene 40 Stearate (80 mg/ml);
135. Poloxamer 407 (160 mg/ml), Polysorbate 80 (80 mg/ml);
136. Poloxamer 407 (160 mg/ml), Propylene Glycol (80 mg/ml);
137. Poloxamer 407 (160 mg/ml), vitamine E TPGS (80 mg/ml);
138. Poloxamer 407 (160 mg/ml), Saccharin sodium (80 mg/ml);
139. Poloxamer 407 (160 mg/ml);
140. Poloxamer 407 (80 mg/ml), Polyoxyethylene 40 Stearate (160 mg/ml);
141. Poloxamer 407 (80 mg/ml), Polyoxyethylene 40 StearatePolysorbate 80 (80 mg/ml);
142. Poloxamer 407 (80 mg/ml), Polysorbate 80 (160 mg/ml);
143. Polyoxyethylene 40 Stearate (80 mg/ml), Polysorbate 80 (160 mg/ml);
144. Polysorbate 80 (160 mg/ml), vitamine E TPGS (80 mg/ml);
145. Polysorbate 80 (160 mg/ml);
146. Polysorbate 80 (80 mg/ml), Propylene Glycol (160 mg/ml);
147. Polysorbate 80 (80 mg/ml), Propylene Glycol (80 mg/ml);
148. Polysorbate 80 (80 mg/ml);

The following combinations of excipients above dissolved at least 24 mg/ml of propofol:
a) Benzalkonium chloride, Poloxamer 237;
b) Benzalkonium chloride, Poloxamer 237, Propylene Glycol;
c) Benzalkonium chloride, Poloxamer 237, Saccharin sodium;
d) Benzethonium Chloride, Poloxamer 237;
e) Benzethonium Chloride, Poloxmer 407;
f) Poloxamer 237, Poloxamer 237;
Poloxamer 237, Poloxmer 407; and Poloxmer 407.

EXAMPLE 11

Propofol containing compositions were prepared as follows. Excipients listed below were added to a glass vessel. Purified water was added followed by 100 mg propofol and 20 mg of citric acid. Water was added as necessary to bring the total volume to 10 milliliters. The final percent concentration (in w/v) for each excipient is listed below in parentheses. The mixtures were stirred at room temperature using a magnetic stirring bar for at least 4 hours over a 24-hour period. The resulting compositions were clear to the naked eye with no visible solids present.
1. poloxamer 188 (8%), polyethylene glycol 400 (4%), propylene glycol (1%)
2. poloxamer 188 (8%), polyethylene glycol 400 (3%), propylene glycol (1%)
3. poloxamer 188 (8%), polyethylene glycol 400 (2%), propylene glycol (1%)
4. poloxamer 188 (8%), polyethylene glycol 400 (3%)
5. poloxamer 188 (8%), polyethylene glycol 400 (2%)
6. poloxamer 188 (8%), polyethylene glycol 400 (4%)
7. poloxamer 188 (7%), polyethylene glycol 400 (3%), propylene glycol (1%)
8. poloxamer 188 (7%), polyethylene glycol 400 (3%)
9. poloxamer 188 (7%), polyethylene glycol 400 (2%), propylene glycol (1%)
10. poloxamer 188 (7%), polyethylene glycol 400 (2%)
11. poloxamer 188 (6%), polyethylene glycol 400 (4%), propylene glycol (1%)
12. poloxamer 188 (6%), polyethylene glycol 400 (4%), propylene glycol (2%)
13. poloxamer 188 (9%), polyethylene glycol 400 (2%)

The propofol containing compositions of Example 11 can also include benzyl alcohol at 0.45% w/v.

EXAMPLE 12

In vitro hemolysis of TPI-213F (1% w/w propofol, 5% w/w poloxamer 188, 4% w/w PEG 400, 1.5% w/w polysorbate 80, 1% w/w propylene glycol, and 2 mg/ml citric acid) was assessed using fresh human whole blood. This study was performed at MDS Pharma Services (Montreal, Canada). Blood was obtained from 2 human volunteers of mixed gender and compatible blood type. Blood samples were pooled and spiked with stock solutions of Diprivan® or TPI-213F in plasma to final concentrations of 10 ug/mL. A saline control was tested to establish auto-lysis of the red blood cells. All samples were incubated at 37° C. At 15, 45 min and 1, 1.5, and 2 hours post-onset of incubation, aliquots (in triplicate) of the whole blood were removed from each sample and centrifuged at 3,200 g for 10 min to obtain plasma. The plasma samples were analyzed for hemoglobin content by measuring the absorbance at 415 nm.

Visual appraisal of hemolysis prior to hemoglobin content determination indicated that there was evidence of hemolysis in all Diprivan® samples at 2 hour following onset of incubation. In contrast, no visual evidence of hemolysis was observed for any TPI-213F samples at any of the time points.

Mean concentrations of hemoglobin in plasma following incubation with increasing amount of Diprivan® and TPI-213F were measured. Consistent with visual appraisal observations, TPI-213F showed lower hemoglobin (p<0.05, the student's t test) concentrations at all time points compared to Diprivan®. This indicates that TPI-213F is milder on red blood cells than Diprivan®.

The hemoglobin concentration in plasma following incubation with the saline control establishes the baseline from auto-lysis of the red blood cell over time. Compared to this baseline, the TPI-213F related samples showed lower hemolysis (p<0.025, the student's t test), indicating that the components in TPI-213F have a stabilizing effect on the red blood cell membrane. In contrast, all Diprivan® samples showed more hemolysis than saline at later time points (after 1 hr incubation, p<0.05).

EXAMPLE 13

A pharmacokinetic study was carried out at MDS Pharma Services in beagle dogs (weight 8-10 kg) to compare TPI-213M (1% propofol w/v, 8% poloxamer 188 w/v, 3% PEG-400 w/v, 1% propylene glycol w/v, 20 mg/ml citric acid, 0.45% benzyl alcohol w/v) and RAPINOVET (a currently marketed lipid based emulsion). All animals were handled according to established guidelines and principles. Administration of all formulations was achieved via slow push over a period of about 1 min through an indwell catheter. All dogs received the same dosing regiment in a cross-over design as follows:

TABLE 9

| Dosing Day | Formulation | Dose (mg/kg) | Dose Volume (mL/kg) | No. of Dogs | Sample collected |
|---|---|---|---|---|---|
| Day 1 | TPI-213M | 6 | 0.6 | 3 | Plasma, blood |
| Day 1 | Rapinovet | 6 | 0.6 | 3 | Plasma, blood |
| Day 8 | Rapinovet | 6 | 0.6 | 3 | Plasma, blood |
| Day 8 | TPI-213M | 6 | 0.6 | 3 | Plasma, blood |

Following dose administration, blood samples were collected at various time points. An aliquot of blood was removed for analysis and the remaining blood was centrifuged at 3,200 g at 4° C. for 10 min. The resulting plasma samples were harvested and stored at −20° C. for analysis of propofol.

The pharmacokinetic parameters calculated for TPI-213M and Rapinovet are shown in Table 10. TPI-213M showed similar plasma concentrations compared to Rapinovet, suggesting that TPI-213M is bioequivalent to Rapinovet. Both formulations also showed similar propofol concentrations and AUC values in blood as in plasma, suggesting that there is no preferential partitioning of the drug into dog red blood cells from either formulation. This is different from what was seen in the rats, pointing to species-related differences in red blood cell partitioning.

Table 10. Mean pharmacokinetic parameters for propofol in plasma and blood following a single intravenous dose of Rapinovet or TPI-213M to Beagle Dogs. Values shown are mean±standard deviation.

| Group | Test Article | Matrix | Dose (mg/kg) | $AUC_{(0-\infty)}$ (ng · hr/mL) | $t_{1/2}$ (hr) | $V_{dss}$ (mL/kg) | CL (mL/hr · kg) |
|---|---|---|---|---|---|---|---|
| 1 | TPI-213M | Plasma | 6 | 929 ± 128 | 0.38 ± 0.15 | 3056 ± 539 | 6553 ± 834 |
| 2 | TPI-213M | Blood | 6 | 746 ± 249 | 0.36 ± 0.07 | 4594 ± 3511 | 9121 ± 4200 |
| 3 | Rapinovet | Plasma | 6 | 1052 ± 255 | 0.41 ± 0.30 | 2509 ± 1476 | 6051 ± 1747 |
| 4 | Rapinovet | Blood | 6 | 892 ± 320 | 0.29 ± 0.03 | 2485 ± 1297 | 7869 ± 4111 |

$AUC_{0-\infty}$: The area under the concentration vs. time curve from time zero to infinity
$t_{1/2}$: Terminal phase half-life
$V_{dss}$: Apparent volume of distribution
CL: Plasma or blood clearance During this pharmacokinetic study, the dogs were also observed for the pharmacological effect from the two formulations, i.e., time to sleep and time to full awakeness. The data suggests that TPI-213M has the same pharmacological effect as Rapinovet.

While this invention has been particularly shown and described with references to preferred embodiments thereof, it will be understood by those skilled in the art that various changes in form and details may be made therein without departing from the scope of the invention encompassed by the appended claims.

We claim:

1. A sterile aqueous pharmaceutical composition for parenteral administration of propofol, said composition consisting essentially of about 1% (w/v) propofol and less than 15% (w/v) excipients, said excipients consisting essentially of:
    7% to 9% (w/v) poloxamer component consisting essentially of Poloxamer 188;
    2% to 4% (w/v) polyethylene glycol;
    less than 1% (w/v) lipid;
    0.5 to 2% (w/v) propylene glycol;
    an antimicrobial agent; and,
    a pH modifier,
    wherein the composition is clear to the naked eye.

2. The composition of claim 1, wherein said polyethylene glycol is polyethylene glycol 400.

3. The composition of claim 1, wherein:
    a) said composition has a particle size diameter of between 25 and 200 nm;
    b) said composition has a particle size diameter of between 50 and 100 nm; or
    c) said composition forms particles of similar particle size.

4. The composition of claim 1, wherein:
    a) said composition does not support microbial growth; or
    b) said composition is microbicidal.

5. The composition of claim 1, wherein said composition is stored in a container having a means for dispensing the composition.

6. A sterile aqueous pharmaceutical composition for parenteral administration of propofol, said composition consisting essentially of about 1% (w/v) propofol and less than 15% (w/v) excipients, said excipients consisting essentially of:
    7% to 9% (w/v) poloxamer component consisting essentially of Poloxamer 188;
    2% to 4% (w/v) polyethylene glycol;
    0.5% to 1% (w/v) propylene glycol;
    an antimicrobial agent;
    a pH modifier;
    and less than 1% (w/v) lipid, wherein the composition is clear to the naked eye.

7. The composition of claim 6, wherein said excipients consist essentially of 8% (w/v) Poloxamer 188; 3% (w/v) polyethylene glycol 400; 1% (w/v) propylene glycol, an antimicrobial agent, and a pH modifier.

* * * * *